(12) United States Patent
Hammer et al.

(10) Patent No.: US 9,238,010 B2
(45) Date of Patent: Jan. 19, 2016

(54) VESICLES AND NANOSTRUCTURES FROM RECOMBINANT PROTEINS

(75) Inventors: Daniel A. Hammer, Villanova, PA (US); Kevin Vargo, Philadelphia, PA (US); Ranganath Parthasarathy, Glenmoore, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 179 days.

(21) Appl. No.: 13/976,796

(22) PCT Filed: Jan. 13, 2012

(86) PCT No.: PCT/US2012/021194
§ 371 (c)(1),
(2), (4) Date: Dec. 17, 2013

(87) PCT Pub. No.: WO2012/097220
PCT Pub. Date: Jul. 19, 2012

(65) Prior Publication Data
US 2014/0105818 A1   Apr. 17, 2014

Related U.S. Application Data

(60) Provisional application No. 61/432,476, filed on Jan. 13, 2011.

(51) Int. Cl.
| | |
|---|---|
| *A61K 9/51* | (2006.01) |
| *A61K 9/127* | (2006.01) |
| *A61K 47/48* | (2006.01) |
| *A61K 38/16* | (2006.01) |
| *A61K 31/7088* | (2006.01) |
| *A61K 38/00* | (2006.01) |
| *A61K 45/06* | (2006.01) |
| *A61K 51/12* | (2006.01) |

(52) U.S. Cl.
CPC ............. *A61K 9/5169* (2013.01); *A61K 9/1272* (2013.01); *A61K 9/1273* (2013.01); *A61K 31/7088* (2013.01); *A61K 38/00* (2013.01); *A61K 38/168* (2013.01); *A61K 45/06* (2013.01); *A61K 47/488* (2013.01); *A61K 51/1251* (2013.01)

(58) Field of Classification Search
None
See application file for complete search history.

(56) References Cited

U.S. PATENT DOCUMENTS

| | | |
|---|---|---|
| 2003/0167531 A1 | 9/2003 | Russell et al. |
| 2007/0006343 A1 | 1/2007 | Moloney et al. |
| 2007/0026484 A1 | 2/2007 | Kinney et al. |
| 2011/0053169 A1 | 3/2011 | Macioszek et al. |
| 2012/0021194 A1 | 1/2012 | Alston et al. |

FOREIGN PATENT DOCUMENTS

| | | | |
|---|---|---|---|
| WO | WO 03/088749 A1 * | 10/2003 | ............. A01N 65/00 |
| WO | 2011/053169 | 5/2011 | |

OTHER PUBLICATIONS

Abell et al., "Role of the Proline Knot Motif in Oleosin Endoplasmic Reticulum Topology and Oil Body Targeting," 1997, *The Plant Cell*, 9:1481-1493.
Abell et al., "Membrane Topology and Sequence Requirements for Oil Body Targeting of Oleosin," 2004, *The Plant Journal*, 37:461-470.
Alexander et al., "Characterization and Modelling of the Hydrophobic Domain of a Sunflower Oleosin," 2002, *Planta*, 214:546-551.
Beaudoin et al., "Targeting and Membrane-Insertion of a Sunflower Oleosin in Vitro and in *Saccharomyces cerevisiae*: The Central Hydrophobic Domain Contains More Than One Signal Sequence, and Directs Oleosin Insertion into the Endoplasmic Reticulum Membrane Using a Signal Anchor Sequence Mechanism," 2002, *Planta*, 215:293-303.
Beaudoin et al., "The Targeting and Accumulation of Ectopically Expressed Oleosin in Non-Seed Tissues of Arabidopis Thaliana," 2000, *Planta*, 210:439-445.
Burzio et al., "Reactivity of Peptidyl-Tyrosine to Hydroxylation and Cross-Linking," 200, *Protein Science*, 10:735-740.
Chiang et al., "Efficient System of Artificial Oil Bodies for Functional Expression and Purification of Recombinant Nattokinase in *Escherichia coli*," 2005, *J. Agric. Food Chem.*, 53:4799-4804.
Chiang et al., "One-Step Purification of Insoluble Hydantoinase Overproduced in *Escherichia coli*," 2007, *Protein Expression and Purification*, 52:14-18.
Chiang et al., "Selective Delivery of Cargo Entitles to Tumor Cells by Nanoscale Artificial Oil Bodies," 2010, *J. Agric. Food Chem.*, 58:11695-11702.
Hsieh et al., "Endoplasmic Reticulum, Oleosins, and Oils in Seeds and Tapetum Cells," 2004, *Plant Physiology*, 136:3427-3434.
Nykiforuk et al., "Transgenic Expression and Recovery of Biologically Active Recombinant Human Insulin from Arabidopsis Thaliana Seeds," 2006, *Plant Biotechnology Journal*, 4:77-85.
Peng et al., "Minimizing the Central Hydrophobic Domain in Oleosin for the Constitution of Artificial Oil Bodies," 2007, *J. Agric. Food Chem.*, 55:5604-5610.
Roberts et al., "Recent Biotechnological Applications Using Oleosins," 2008, *The Open Biotechnology Journal*, 2:13-21.
Roy et al., "Chimeric Fibronectin Matrix Mimetic as a Functional Growth- and Migration-Promoting Adhesive Substrate," 2011, *Biomaterials*, 32:2077-2087.
International Search Report for PCT/US12/21194, issued Jul. 30, 2012.

* cited by examiner

*Primary Examiner* — Suzanne M Noakes
*Assistant Examiner* — Jae W Lee
(74) *Attorney, Agent, or Firm* — Saul Ewing LLP; Kathryn Doyle; Domingos J. Silva

(57) ABSTRACT

The present invention includes a composition comprising at least one oleosin-like protein. The present invention also includes a composition comprising a vesicle comprising at least one oleosin-like protein.

13 Claims, 21 Drawing Sheets

Fig. 2

"Oleosin-1" (SEQ ID NO:1)
MATTTYDRHHVTTQPQYRHDQHTGDRLTHPQRQQQGPSTGKIMVIMALLPITGILFGL
AGITLVGTVIGLALATPLFVIFSPVIVPAMIAIGLAVTGFLTSGTFGLTGLSSLSYLFNMVRRS
TMSVPVQRDYVKGKLQDVGEYTGQKTKDLGQKIQHTAHEMGDQGQGQGQGGKEGRKE
GGKLEHHHHHH Oleosin-Hydrophobic ("oleosin-2"; SEQ ID NO:2)
MRHDQHTGDRLTHPQRQQQGPSTGKIMVIMALLPITGILFGLAGITLVGTVIGLALATPLFV
IFSPVIVPAMIAIGLAVTGFLTSGTFGLTGLSSLSYLFNMVRRSTMSVPVQRDYVKGKLQDVG
EYTGQKTKDLGQKIQHTAHEMGDQGLEHHHHHH Oleosin-Hydrophilic ("oleosin-3"; SEQ ID NO:3)
MATTTYDRHHVTTQPQYRHDQHTGDRLTHPQRQQQGPSTGKITGILFGLTGITLVGTVIG
LALATPLFVIFSPVIVPAMIAIGLAVTGFLTRSTMSVPVQRDYVKGKLQDVGEYTG
QKTKDLGQKIQHTAHEMGDQGQGQGQGGKEGRKEGGKLEHHHHHH

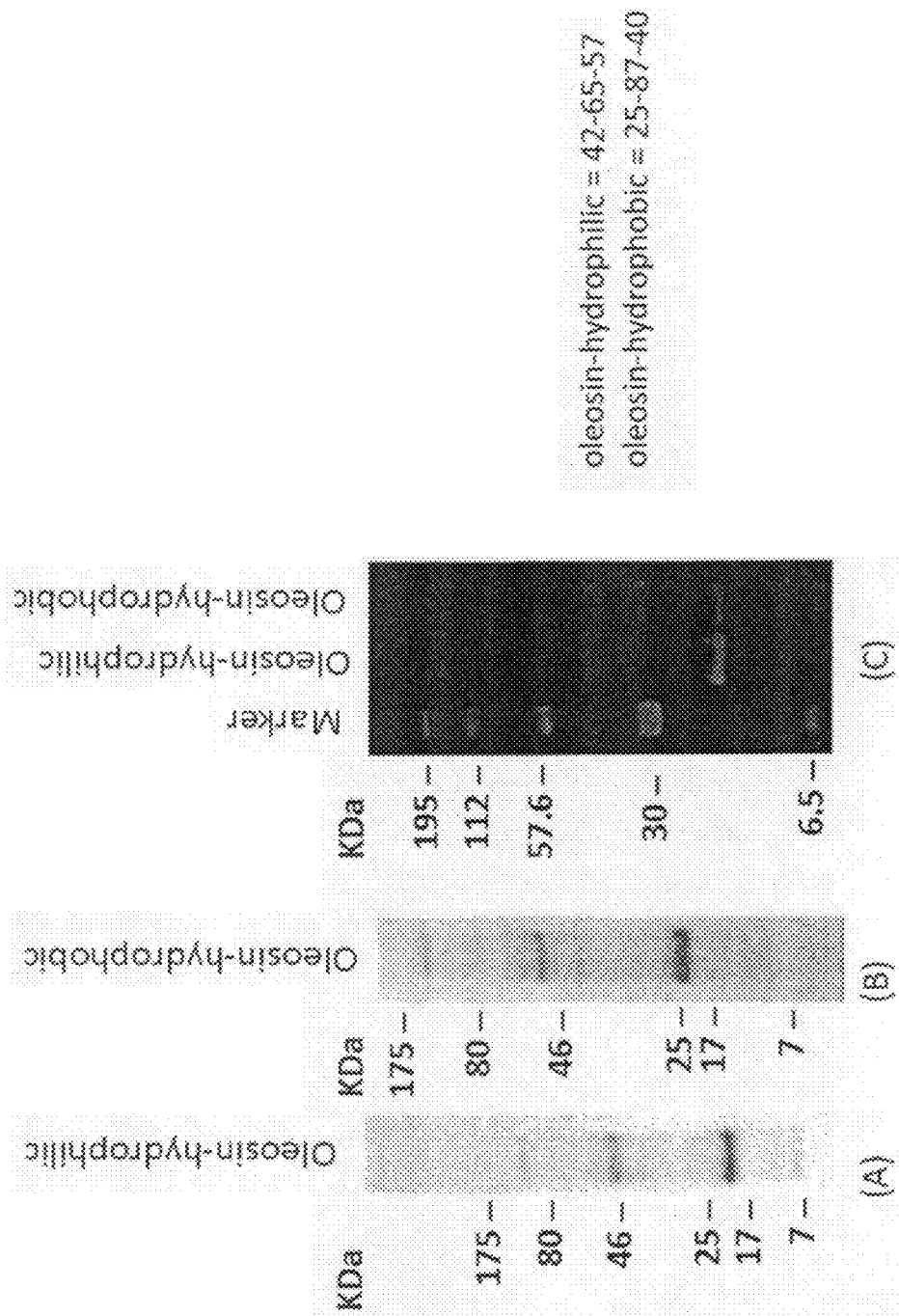

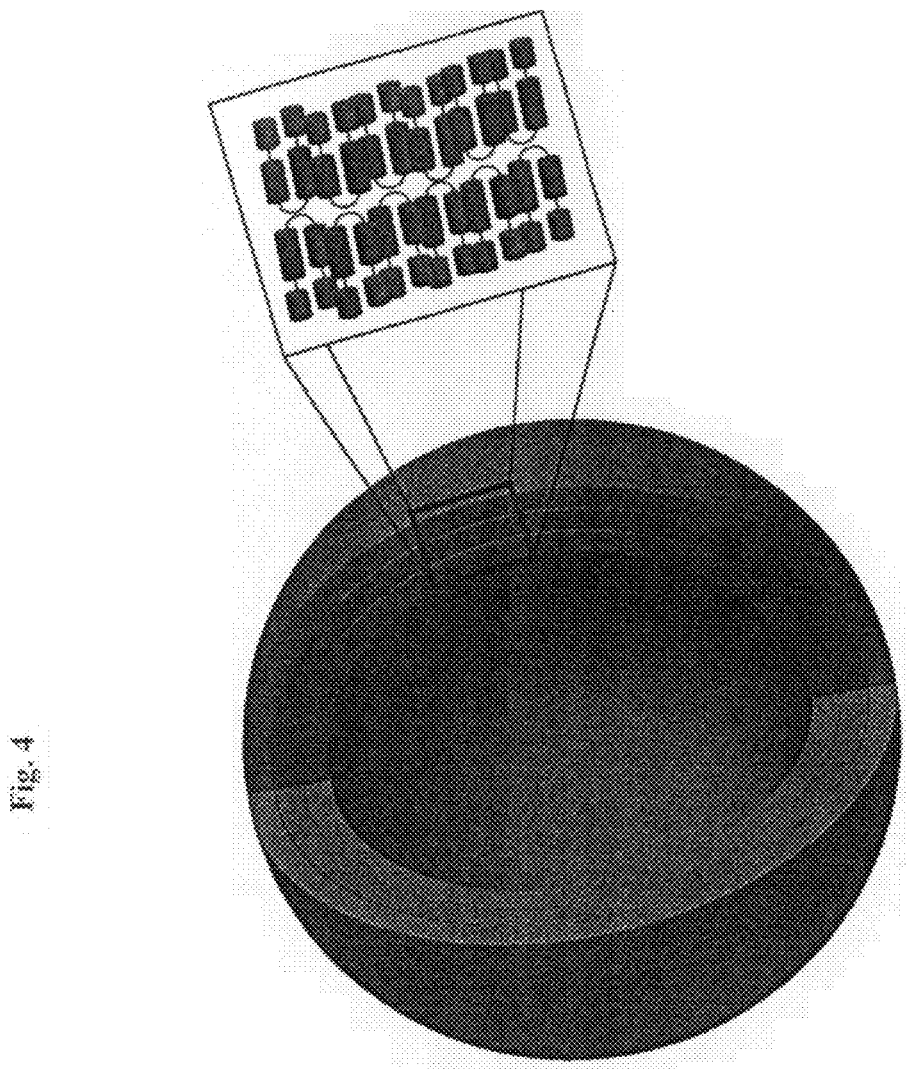
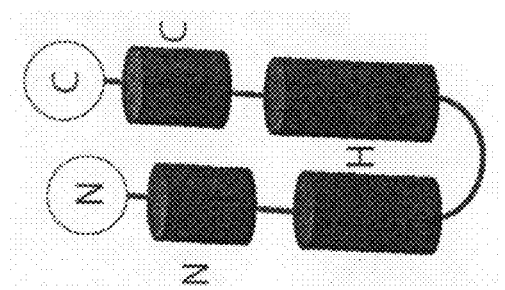
Fig. 4

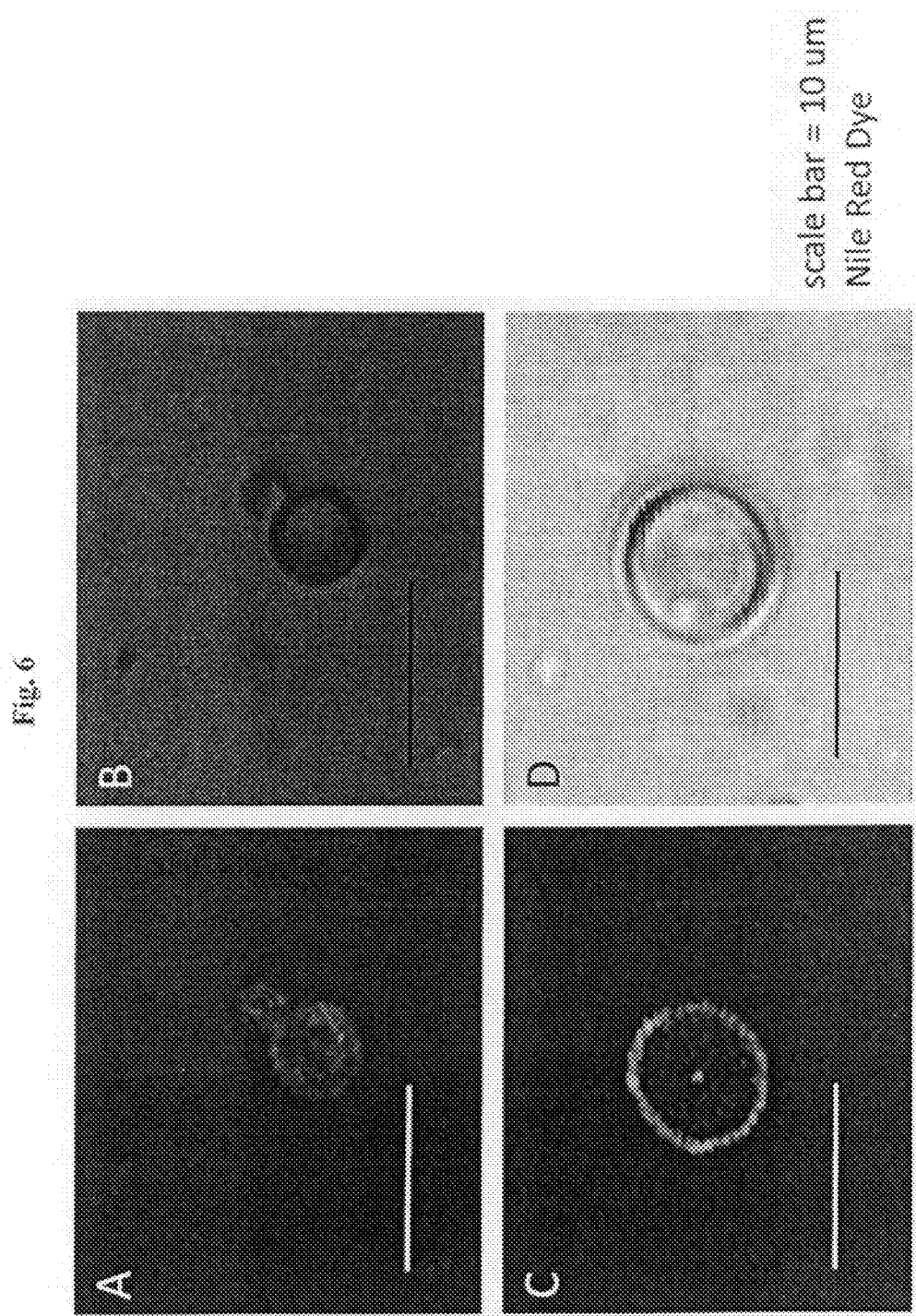

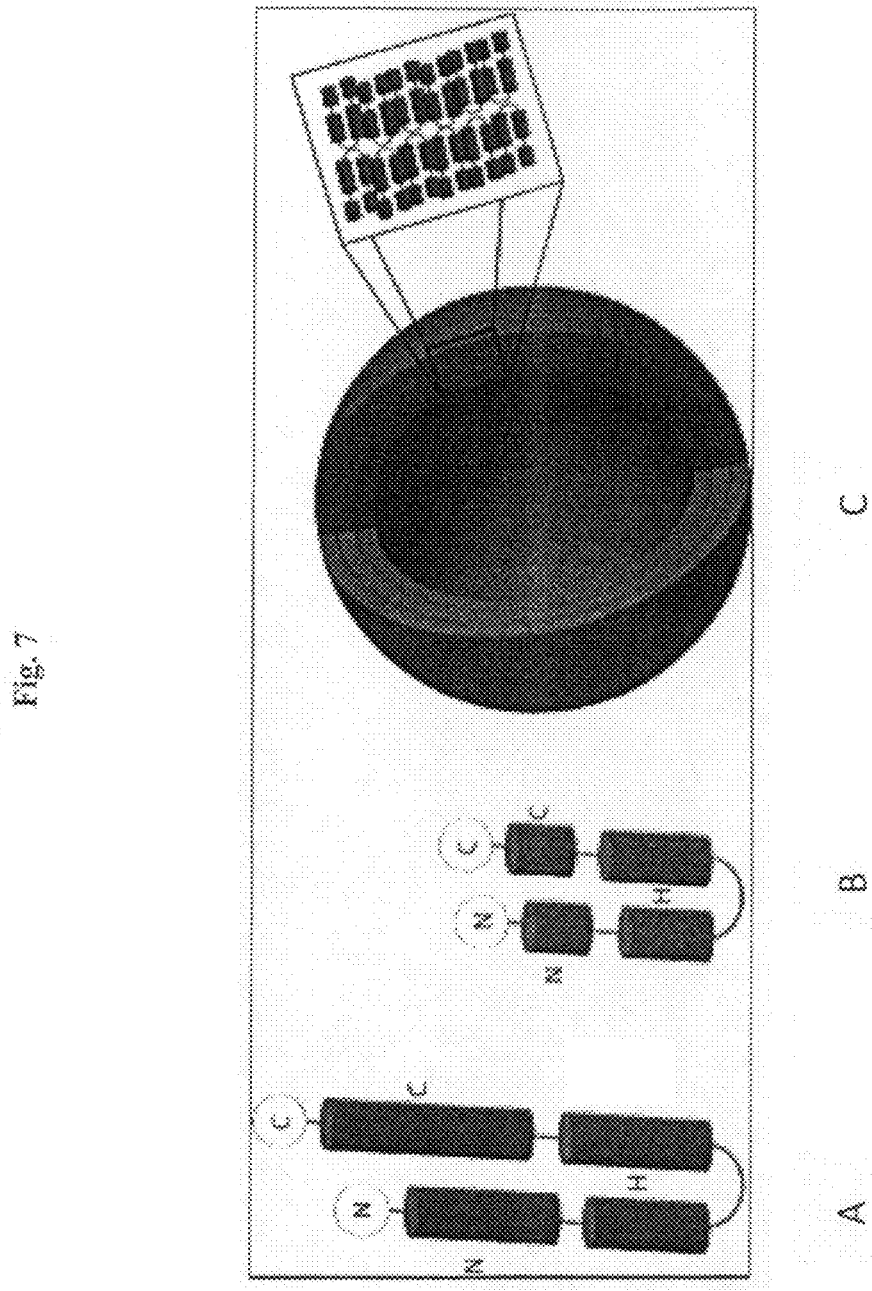

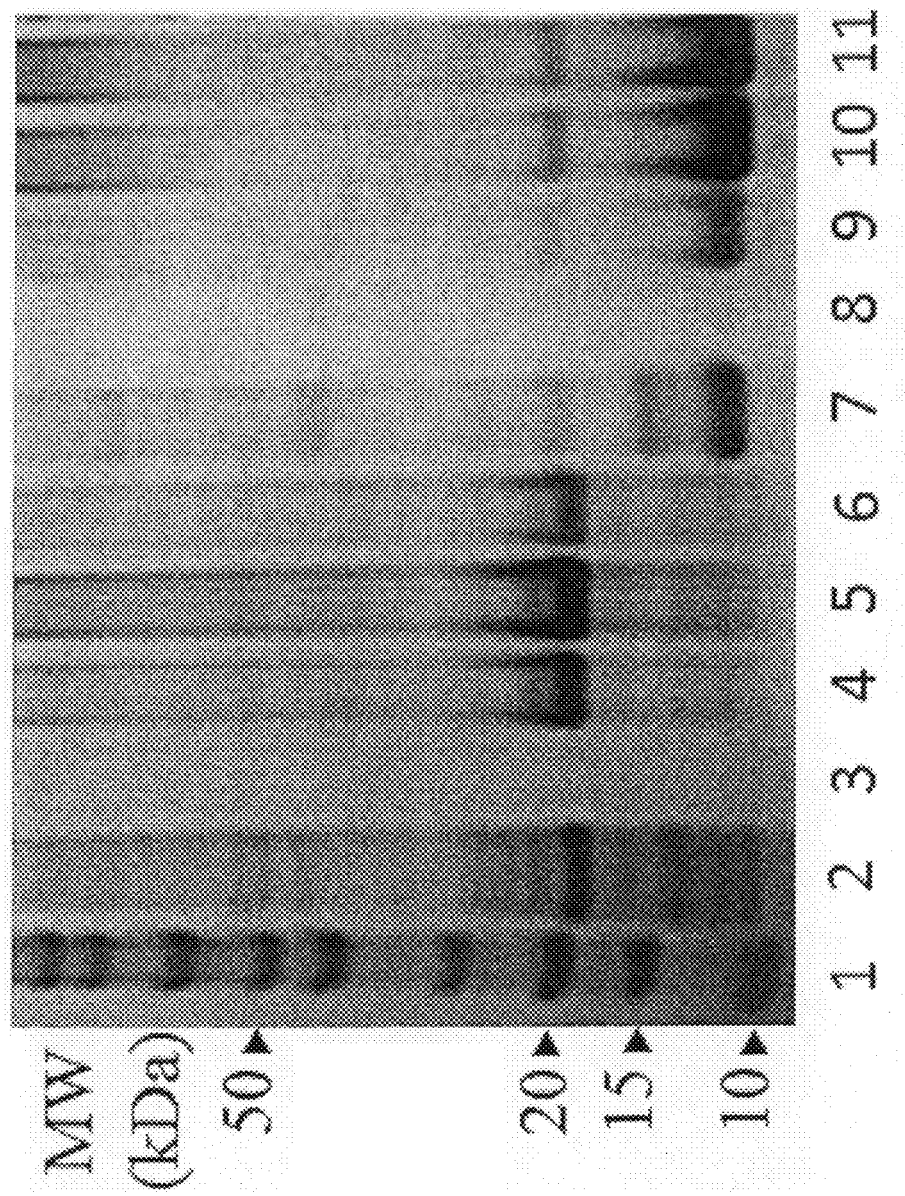

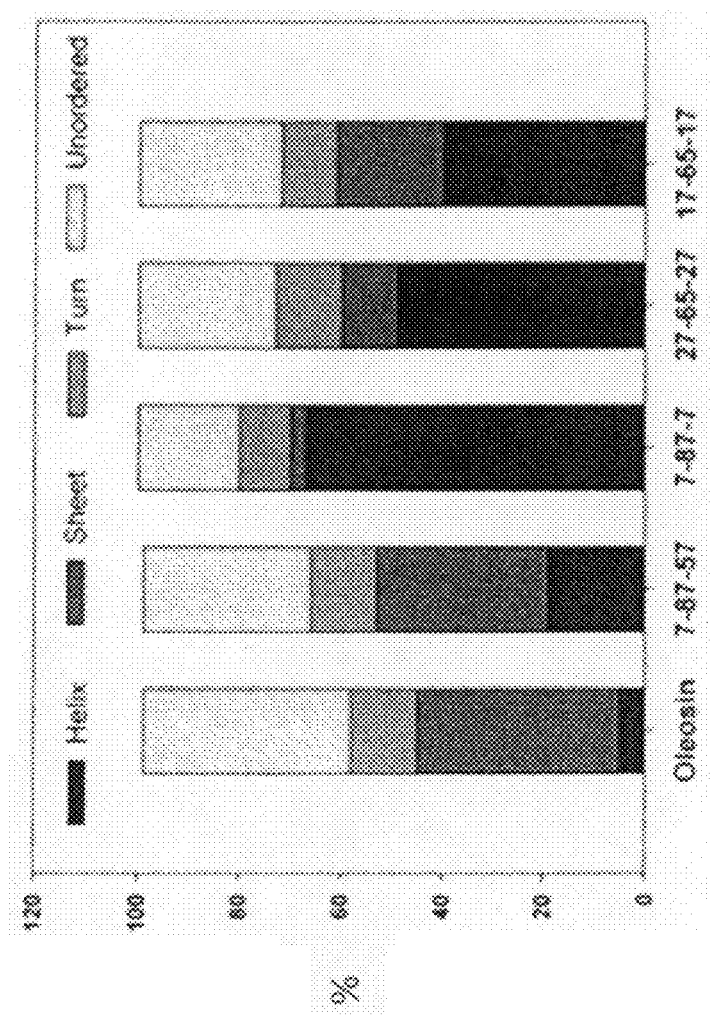

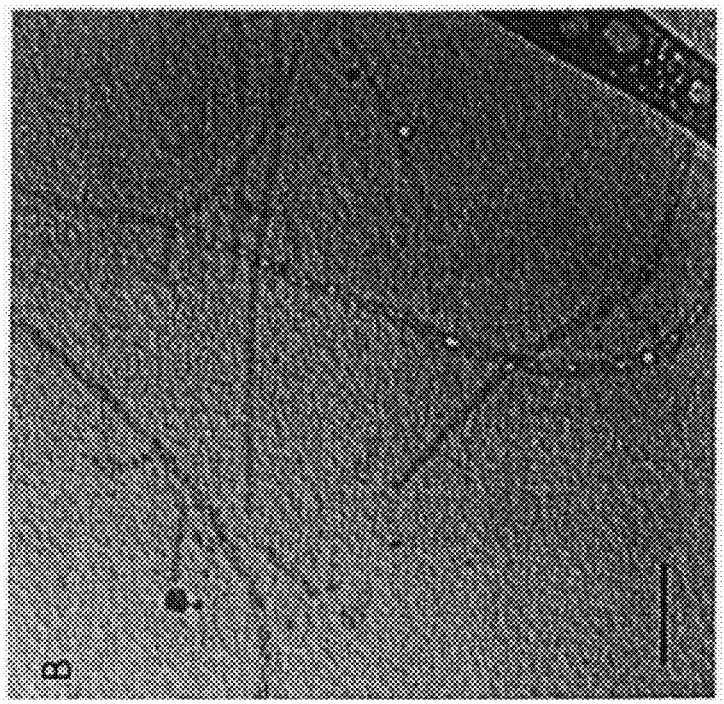
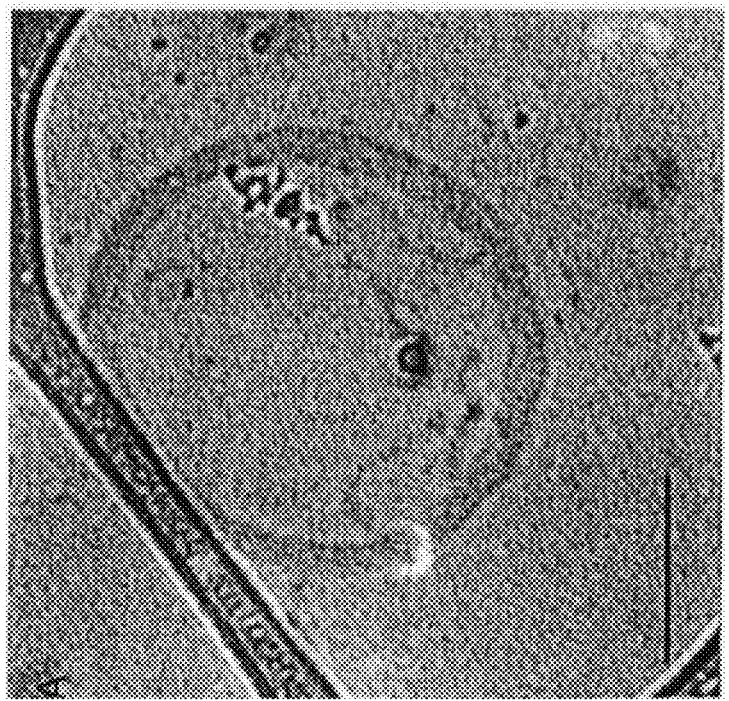

| Molecule | Expected Molecular Weight (Da) | Estimated PI |
|---|---|---|
| 42-87-57 (Oleo-WT) | 20785 | 9.95 |
| 7-87-7 | 11401 | 10.03 |
| 7-87-57 | 16650 | 9.94 |
| 42-87-7 | 15609 | 10.01 |
| 12-87-27 | 14174 | 10.14 |
| 7-87-12 | 11955 | 10.53 |
| 12-87-12 | 12553 | 10.9 |
| 22-87-37 | 16450 | 10.07 |
| 42-87-32 | 18261 | 10.06 |
| 27-87-12 | 14265 | 10.58 |
| 22-87-12 | 13565 | 10.89 |
| 7-65-7 | 10820 | 6.408 |
| 12-65-12 | 11942 | 9.501 |
| 17-65-17 (Oleo-M1) | 13082 | 6.851 |
| 27-65-27 | 15164 | 9.232 |
| 42-65-7 | 14898 | 7.043 |
| 7-65-57 | 15938 | 8.053 |

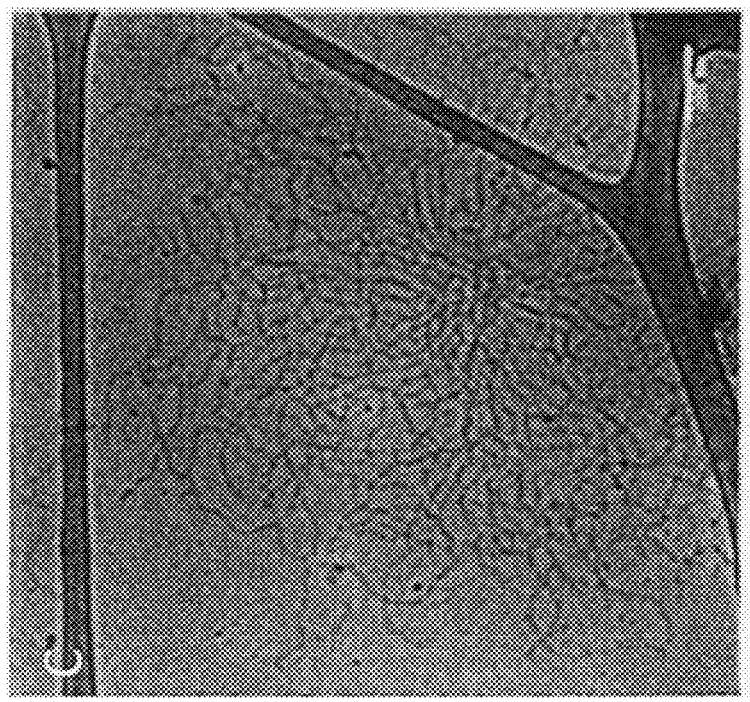
Fig. 14C  27-65-27

SEQUENCE LISTING

```
<160> NUMBER OF SEQ ID NOS: 30

<210> SEQ ID NO 1
<211> LENGTH: 192
<212> TYPE: PRT
<213> ORGANISM: Artificial Sequence
<220> FEATURE:
<223> OTHER INFORMATION: chemically synthesized

<400> SEQUENCE: 1

Met Ala Thr Thr Thr Tyr Asp Arg His His Val Thr Thr Thr Gln Pro
1               5                   10                  15

Gln Tyr Arg His Asp Gln His Thr Gly Asp Arg Leu Thr His Pro Gln
                20                  25                  30

Arg Gln Gln Gln Gly Pro Ser Thr Gly Lys Ile Met Val Ile Met Ala
            35                  40                  45
```

Leu Leu Pro Ile Thr Gly Ile Leu Phe Gly Leu Ala Gly Ile Thr Leu
            50                  55                  60

Val Gly Thr Val Ile Gly Leu Ala Leu Ala Thr Pro Leu Phe Val Ile
 65                  70                  75                  80

Phe Ser Pro Val Ile Val Pro Ala Met Ile Ala Ile Gly Leu Ala Val
                 85                  90                  95

Thr Gly Phe Leu Thr Ser Gly Thr Phe Gly Leu Thr Gly Leu Ser Ser
            100                 105                 110

Leu Ser Tyr Leu Phe Asn Met Val Arg Arg Ser Thr Met Ser Val Pro
            115                 120                 125

Val Gln Arg Asp Tyr Val Lys Gly Lys Leu Gln Asp Val Gly Glu Tyr
130                 135                 140

Thr Gly Gln Lys Thr Lys Asp Leu Gly Gln Lys Ile Gln His Thr Ala
145                 150                 155                 160

His Glu Met Gly Asp Gln Gly Gln Gln Gly Gln Gly Gln Gly Gly Lys
                165                 170                 175

Glu Gly Arg Lys Glu Gly Gly Lys Leu Glu His His His His His His
            180                 185                 190

<210> SEQ ID NO 2
<211> LENGTH: 158
<212> TYPE: PRT
<213> ORGANISM: Artificial Sequence
<220> FEATURE:
<223> OTHER INFORMATION: chemically synthesized

<400> SEQUENCE: 2

Met Arg His Asp Gln His Thr Gly Asp Arg Leu Thr His Pro Gln Arg
 1                   5                  10                  15

Gln Gln Gln Gly Pro Ser Thr Gly Lys Ile Met Val Ile Met Ala Leu
                20                  25                  30

Leu Pro Ile Thr Gly Ile Leu Phe Gly Leu Ala Gly Ile Thr Leu Val
            35                  40                  45

Gly Thr Val Ile Gly Leu Ala Leu Ala Thr Pro Leu Phe Val Ile Phe
 50                  55                  60

Ser Pro Val Ile Val Pro Ala Met Ile Ala Ile Gly Leu Ala Val Thr
 65                  70                  75                  80

Gly Phe Leu Thr Ser Gly Thr Phe Gly Leu Thr Gly Leu Ser Ser Leu
                85                  90                  95

Ser Tyr Leu Phe Asn Met Val Arg Arg Ser Thr Met Ser Val Pro Val
            100                 105                 110

Gln Arg Asp Tyr Val Lys Gly Lys Leu Gln Asp Val Gly Glu Tyr Thr
        115                 120                 125

Gly Gln Lys Thr Lys Asp Leu Gly Gln Lys Ile Gln His Thr Ala His
130                 135                 140

Glu Met Gly Asp Gln Gly Leu Glu His His His His His His
145                 150                 155

<210> SEQ ID NO 3
<211> LENGTH: 170
<212> TYPE: PRT
<213> ORGANISM: Artificial Sequence
<220> FEATURE:
<223> OTHER INFORMATION: chemically synthesized

<400> SEQUENCE: 3

Met Ala Thr Thr Thr Tyr Asp Arg His His Val Thr Thr Gln Pro
 1                   5                  10                  15

-continued

Gln Tyr Arg His Asp Gln His Thr Gly Asp Arg Leu Thr His Pro Gln
             20                  25                  30

Arg Gln Gln Gln Gly Pro Ser Thr Gly Lys Ile Thr Gly Ile Leu Phe
         35                  40                  45

Gly Leu Thr Gly Ile Thr Leu Val Gly Thr Val Ile Gly Leu Ala Leu
     50                  55                  60

Ala Thr Pro Leu Phe Val Ile Phe Ser Pro Val Ile Val Pro Ala Met
 65                  70                  75                  80

Ile Ala Ile Gly Leu Ala Val Thr Gly Phe Leu Thr Ser Gly Thr Phe
                 85                  90                  95

Gly Leu Thr Arg Ser Thr Met Ser Val Pro Val Gln Arg Asp Tyr Val
            100                 105                 110

Lys Gly Lys Leu Gln Asp Val Gly Glu Tyr Thr Gly Gln Lys Thr Lys
        115                 120                 125

Asp Leu Gly Gln Lys Ile Gln His Thr Ala His Glu Met Gly Asp Gln
130                 135                 140

Gly Gln Gly Gln Gly Gln Gly Gly Lys Glu Gly Arg Lys Glu Gly
145                 150                 155                 160

Gly Lys Leu Glu His His His His His His
                165                 170

<210> SEQ ID NO 4
<211> LENGTH: 4
<212> TYPE: PRT
<213> ORGANISM: Artificial Sequence
<220> FEATURE:
<223> OTHER INFORMATION: chemically synthesized

<400> SEQUENCE: 4

Arg Gly Asp Ser
1

<210> SEQ ID NO 5
<211> LENGTH: 5
<212> TYPE: PRT
<213> ORGANISM: Artificial Sequence
<220> FEATURE:
<223> OTHER INFORMATION: chemically synthesized

<400> SEQUENCE: 5

Pro His Ser Arg Asn
1               5

<210> SEQ ID NO 6
<211> LENGTH: 9
<212> TYPE: PRT
<213> ORGANISM: Artificial Sequence
<220> FEATURE:
<223> OTHER INFORMATION: chemically synthesized

<400> SEQUENCE: 6

Arg Lys Lys Arg Arg Gln Arg Arg Arg
1               5

<210> SEQ ID NO 7
<211> LENGTH: 5
<212> TYPE: PRT
<213> ORGANISM: Artificial Sequence
<220> FEATURE:
<223> OTHER INFORMATION: chemically synthesized

<400> SEQUENCE: 7

```
Gly Gly Gly Gly Ser
1               5

<210> SEQ ID NO 8
<211> LENGTH: 5
<212> TYPE: PRT
<213> ORGANISM: Artificial Sequence
<220> FEATURE:
<223> OTHER INFORMATION: chemically synthesized

<400> SEQUENCE: 8

Asp Asp Asp Asp Lys
1               5

<210> SEQ ID NO 9
<211> LENGTH: 4
<212> TYPE: PRT
<213> ORGANISM: Artificial Sequence
<220> FEATURE:
<223> OTHER INFORMATION: chemically synthesized

<400> SEQUENCE: 9

Ile Glu Gly Arg
1

<210> SEQ ID NO 10
<211> LENGTH: 6
<212> TYPE: PRT
<213> ORGANISM: Artificial Sequence
<220> FEATURE:
<223> OTHER INFORMATION: chemically synthesized

<400> SEQUENCE: 10

Glu Asn Leu Tyr Gln Gly
1               5

<210> SEQ ID NO 11
<211> LENGTH: 5
<212> TYPE: PRT
<213> ORGANISM: Artificial Sequence
<220> FEATURE:
<223> OTHER INFORMATION: chemically synthesized

<400> SEQUENCE: 11

Leu Val Pro Arg Gly
1               5

<210> SEQ ID NO 12
<211> LENGTH: 5
<212> TYPE: PRT
<213> ORGANISM: Artificial Sequence
<220> FEATURE:
<223> OTHER INFORMATION: chemically synthesized

<400> SEQUENCE: 12

Leu Pro Glu Thr Gly
1               5

<210> SEQ ID NO 13
<211> LENGTH: 108
<212> TYPE: PRT
<213> ORGANISM: Artificial Sequence
<220> FEATURE:
<223> OTHER INFORMATION: chemically synthesized

<400> SEQUENCE: 13
```

Met Gly Ser Pro Ser Thr Gly Lys Ile Met Val Ile Met Ala Leu Leu
1               5                   10                  15

Pro Ile Thr Gly Ile Leu Phe Gly Leu Ala Gly Ile Thr Leu Val Gly
            20                  25                  30

Thr Val Ile Gly Leu Ala Leu Ala Thr Pro Leu Phe Val Ile Phe Ser
            35                  40                  45

Pro Val Ile Val Pro Ala Met Ile Ala Ile Gly Leu Ala Val Thr Gly
        50                  55                  60

Phe Leu Thr Ser Gly Thr Phe Gly Leu Thr Gly Leu Ser Ser Leu Ser
65                  70                  75                  80

Tyr Leu Phe Asn Met Val Arg Arg Ser Thr Met Ser Val Pro Val Gln
                85                  90                  95

Arg Asp Tyr Val Leu Glu His His His His His
            100                 105

<210> SEQ ID NO 14
<211> LENGTH: 158
<212> TYPE: PRT
<213> ORGANISM: Artificial Sequence
<220> FEATURE:
<223> OTHER INFORMATION: chemically synthesized

<400> SEQUENCE: 14

Met Gly Ser Pro Ser Thr Gly Lys Ile Met Val Ile Met Ala Leu Leu
1               5                   10                  15

Pro Ile Thr Gly Ile Leu Phe Gly Leu Ala Gly Ile Thr Leu Val Gly
            20                  25                  30

Thr Val Ile Gly Leu Ala Leu Ala Thr Pro Leu Phe Val Ile Phe Ser
            35                  40                  45

Pro Val Ile Val Pro Ala Met Ile Ala Ile Gly Leu Ala Val Thr Gly
        50                  55                  60

Phe Leu Thr Ser Gly Thr Phe Gly Leu Thr Gly Leu Ser Ser Leu Ser
65                  70                  75                  80

Tyr Leu Phe Asn Met Val Arg Arg Ser Thr Met Ser Val Pro Val Gln
                85                  90                  95

Arg Asp Tyr Val Lys Gly Lys Leu Gln Asp Val Gly Glu Tyr Thr Gly
            100                 105                 110

Gln Lys Thr Lys Asp Leu Gly Gln Lys Ile Gln His Thr Ala His Glu
        115                 120                 125

Met Gly Asp Gln Gly Gln Gly Gln Gly Gln Gly Gly Lys Glu Gly
        130                 135                 140

Arg Lys Glu Gly Gly Lys Leu Glu His His His His His
145                 150                 155

<210> SEQ ID NO 15
<211> LENGTH: 143
<212> TYPE: PRT
<213> ORGANISM: Artificial Sequence
<220> FEATURE:
<223> OTHER INFORMATION: chemically synthesized

<400> SEQUENCE: 15

Met Gly Ser Thr Thr Thr Tyr Asp Arg His His Val Thr Thr Gln
1               5                   10                  15

Pro Gln Tyr Arg His Asp Gln His Thr Gly Asp Arg Leu Thr His Pro
            20                  25                  30

Gln Arg Gln Gln Gln Gly Pro Ser Thr Gly Lys Ile Met Val Ile Met
            35                  40                  45

```
Ala Leu Leu Pro Ile Thr Gly Ile Leu Phe Gly Leu Ala Gly Ile Thr
    50                  55                  60

Leu Val Gly Thr Val Ile Gly Leu Ala Leu Ala Thr Pro Leu Phe Val
65                  70                  75                  80

Ile Phe Ser Pro Val Ile Val Pro Ala Met Ile Ala Ile Gly Leu Ala
                85                  90                  95

Val Thr Gly Phe Leu Thr Ser Gly Thr Phe Gly Leu Thr Gly Leu Ser
            100                 105                 110

Ser Leu Ser Tyr Leu Phe Asn Met Val Arg Arg Ser Thr Met Ser Val
        115                 120                 125

Pro Val Gln Arg Asp Tyr Val Leu Glu His His His His His
    130                 135                 140
```

<210> SEQ ID NO 16
<211> LENGTH: 133
<212> TYPE: PRT
<213> ORGANISM: Artificial Sequence
<220> FEATURE:
<223> OTHER INFORMATION: chemically synthesized

<400> SEQUENCE: 16

```
Met Gly Ser Arg Gln Gln Gln Gly Pro Ser Thr Gly Lys Ile Met Val
1               5                   10                  15

Ile Met Ala Leu Leu Pro Ile Thr Gly Ile Leu Phe Gly Leu Ala Gly
            20                  25                  30

Ile Thr Leu Val Gly Thr Val Ile Gly Leu Ala Leu Ala Thr Pro Leu
        35                  40                  45

Phe Val Ile Phe Ser Pro Val Ile Val Pro Ala Met Ile Ala Ile Gly
    50                  55                  60

Leu Ala Val Thr Gly Phe Leu Thr Ser Gly Thr Phe Gly Leu Thr Gly
65                  70                  75                  80

Leu Ser Ser Leu Ser Tyr Leu Phe Asn Met Val Arg Arg Ser Thr Met
                85                  90                  95

Ser Val Pro Val Gln Arg Asp Tyr Val Lys Gly Lys Leu Gln Asp Val
            100                 105                 110

Gly Glu Tyr Thr Gly Gln Lys Thr Lys Asp Leu Gly Gln Leu Glu His
        115                 120                 125

His His His His His
    130
```

<210> SEQ ID NO 17
<211> LENGTH: 113
<212> TYPE: PRT
<213> ORGANISM: Artificial Sequence
<220> FEATURE:
<223> OTHER INFORMATION: chemically synthesized

<400> SEQUENCE: 17

```
Met Gly Ser Pro Ser Thr Gly Lys Ile Met Val Ile Met Ala Leu Leu
1               5                   10                  15

Pro Ile Thr Gly Ile Leu Phe Gly Leu Ala Gly Ile Thr Leu Val Gly
            20                  25                  30

Thr Val Ile Gly Leu Ala Leu Ala Thr Pro Leu Phe Val Ile Phe Ser
        35                  40                  45

Pro Val Ile Val Pro Ala Met Ile Ala Ile Gly Leu Ala Val Thr Gly
    50                  55                  60

Phe Leu Thr Ser Gly Thr Phe Gly Leu Thr Gly Leu Ser Ser Leu Ser
```

```
                65                  70                  75                  80
Tyr Leu Phe Asn Met Val Arg Arg Ser Thr Met Ser Val Pro Val Gln
                    85                  90                  95

Arg Asp Tyr Val Lys Gly Lys Leu Gln Leu Glu His His His His
            100                 105                 110

His
```

<210> SEQ ID NO 18
<211> LENGTH: 118
<212> TYPE: PRT
<213> ORGANISM: Artificial Sequence
<220> FEATURE:
<223> OTHER INFORMATION: chemically synthesized

<400> SEQUENCE: 18

```
Met Gly Ser Arg Gln Gln Gln Gly Pro Ser Thr Gly Lys Ile Met Val
1               5                   10                  15

Ile Met Ala Leu Leu Pro Ile Thr Gly Ile Leu Phe Gly Leu Ala Gly
                20                  25                  30

Ile Thr Leu Val Gly Thr Val Ile Gly Leu Ala Leu Ala Thr Pro Leu
            35                  40                  45

Phe Val Ile Phe Ser Pro Val Ile Val Pro Ala Met Ile Ala Ile Gly
    50                  55                  60

Leu Ala Val Thr Gly Phe Leu Thr Ser Gly Thr Phe Gly Leu Thr Gly
65                  70                  75                  80

Leu Ser Ser Leu Ser Tyr Leu Phe Asn Met Val Arg Arg Ser Thr Met
                85                  90                  95

Ser Val Pro Val Gln Arg Asp Tyr Val Lys Gly Lys Leu Gln Leu Glu
            100                 105                 110

His His His His His His
        115
```

<210> SEQ ID NO 19
<211> LENGTH: 153
<212> TYPE: PRT
<213> ORGANISM: Artificial Sequence
<220> FEATURE:
<223> OTHER INFORMATION: chemically synthesized

<400> SEQUENCE: 19

```
Met Gly Ser His Thr Gly Asp Arg Leu Thr His Pro Gln Arg Gln Gln
1               5                   10                  15

Gln Gly Pro Ser Thr Gly Lys Ile Met Val Ile Met Ala Leu Leu Pro
                20                  25                  30

Ile Thr Gly Ile Leu Phe Gly Leu Ala Gly Ile Thr Leu Val Gly Thr
            35                  40                  45

Val Ile Gly Leu Ala Leu Ala Thr Pro Leu Phe Val Ile Phe Ser Pro
    50                  55                  60

Val Ile Val Pro Ala Met Ile Ala Ile Gly Leu Ala Val Thr Gly Phe
65                  70                  75                  80

Leu Thr Ser Gly Thr Phe Gly Leu Thr Gly Leu Ser Ser Leu Ser Tyr
                85                  90                  95

Leu Phe Asn Met Val Arg Arg Ser Thr Met Ser Val Pro Val Gln Arg
            100                 105                 110

Asp Tyr Val Lys Gly Lys Leu Gln Asp Val Gly Glu Tyr Thr Gly Gln
        115                 120                 125

Lys Thr Lys Asp Leu Gly Gln Lys Ile Gln His Thr Ala His Glu Met
```

Gly Leu Glu His His His His His
145                 150

<210> SEQ ID NO 20
<211> LENGTH: 167
<212> TYPE: PRT
<213> ORGANISM: Artificial Sequence
<220> FEATURE:
<223> OTHER INFORMATION: chemically synthesized

<400> SEQUENCE: 20

Gly Ser Thr Thr Thr Tyr Asp Arg His His Val Thr Thr Thr Gln Pro
1               5                   10                  15

Gln Tyr Arg His Asp Gln His Thr Gly Asp Arg Leu Thr His Pro Gln
            20                  25                  30

Arg Gln Gln Gln Gly Pro Ser Thr Gly Lys Ile Met Val Ile Met Ala
        35                  40                  45

Leu Leu Pro Ile Thr Gly Ile Leu Phe Gly Leu Ala Gly Ile Thr Leu
    50                  55                  60

Val Gly Thr Val Ile Gly Leu Ala Leu Ala Thr Pro Leu Phe Val Ile
65                  70                  75                  80

Phe Ser Pro Val Ile Val Pro Ala Met Ile Ala Ile Gly Leu Ala Val
                85                  90                  95

Thr Gly Phe Leu Thr Ser Gly Thr Phe Gly Leu Thr Gly Leu Ser Ser
            100                 105                 110

Leu Ser Tyr Leu Phe Asn Met Val Arg Arg Ser Thr Met Ser Val Pro
        115                 120                 125

Val Gln Arg Asp Tyr Val Lys Gly Lys Leu Gln Asp Val Gly Glu Tyr
    130                 135                 140

Thr Gly Gln Lys Thr Lys Asp Leu Gly Gln Lys Ile Gln His Thr Leu
145                 150                 155                 160

Glu His His His His His
            165

<210> SEQ ID NO 21
<211> LENGTH: 101
<212> TYPE: PRT
<213> ORGANISM: Artificial Sequence
<220> FEATURE:
<223> OTHER INFORMATION: chemically synthesized

<400> SEQUENCE: 21

Met Gly Leu Asn Asp Ile Phe Glu Ala Gln Lys Ile Glu Trp His Glu
1               5                   10                  15

Gly Ser Pro Ser Thr Gly Lys Ile Met Gly Ile Leu Phe Gly Leu Thr
            20                  25                  30

Gly Ile Thr Leu Val Gly Thr Val Ile Gly Leu Ala Leu Ala Thr Pro
        35                  40                  45

Leu Phe Val Ile Phe Ser Pro Val Ile Val Pro Ala Met Ile Ala Ile
    50                  55                  60

Gly Leu Ala Val Thr Gly Phe Leu Thr Ser Gly Thr Phe Gly Leu Thr
65                  70                  75                  80

Arg Ser Thr Met Ser Val Pro Val Gln Arg Asp Tyr Val Leu Glu His
                85                  90                  95

His His His His His
            100

```
<210> SEQ ID NO 22
<211> LENGTH: 111
<212> TYPE: PRT
<213> ORGANISM: Artificial Sequence
<220> FEATURE:
<223> OTHER INFORMATION: chemically synthesized

<400> SEQUENCE: 22

Met Gly Leu Asn Asp Ile Phe Glu Ala Gln Lys Ile Glu Trp His Glu
1               5                   10                  15

Gly Ser Arg Gln Gln Gln Gly Pro Ser Thr Gly Lys Ile Thr Gly Ile
            20                  25                  30

Leu Phe Gly Leu Thr Gly Ile Thr Leu Val Gly Thr Val Ile Gly Leu
        35                  40                  45

Ala Leu Ala Thr Pro Leu Phe Val Ile Phe Ser Pro Val Ile Val Pro
    50                  55                  60

Ala Met Ile Ala Ile Gly Leu Ala Val Thr Gly Phe Leu Thr Ser Gly
65                  70                  75                  80

Thr Phe Gly Leu Thr Arg Ser Thr Met Ser Val Pro Val Gln Arg Asp
                85                  90                  95

Tyr Val Lys Gly Lys Leu Gln Leu Glu His His His His His His
            100                 105                 110

<210> SEQ ID NO 23
<211> LENGTH: 121
<212> TYPE: PRT
<213> ORGANISM: Artificial Sequence
<220> FEATURE:
<223> OTHER INFORMATION: chemically synthesized

<400> SEQUENCE: 23

Met Gly Leu Asn Asp Ile Phe Glu Ala Gln Lys Ile Glu Trp His Glu
1               5                   10                  15

Gly Ser Leu Thr His Pro Gln Arg Gln Gln Gly Pro Ser Thr Gly
            20                  25                  30

Lys Ile Thr Gly Ile Leu Phe Gly Leu Thr Gly Ile Thr Leu Val Gly
            35                  40                  45

Thr Val Ile Gly Leu Ala Leu Ala Thr Pro Leu Phe Val Ile Phe Ser
    50                  55                  60

Pro Val Ile Val Pro Ala Met Ile Ala Ile Gly Leu Ala Val Thr Gly
65                  70                  75                  80

Phe Leu Thr Ser Gly Thr Phe Gly Leu Thr Arg Ser Thr Met Ser Val
                85                  90                  95

Pro Val Gln Arg Asp Tyr Val Lys Gly Lys Leu Gln Asp Val Gly Glu
            100                 105                 110

Tyr Leu Glu His His His His His His
        115                 120

<210> SEQ ID NO 24
<211> LENGTH: 139
<212> TYPE: PRT
<213> ORGANISM: Artificial Sequence
<220> FEATURE:
<223> OTHER INFORMATION: chemically synthesized

<400> SEQUENCE: 24

Met Gly Leu Asn Asp Ile Phe Glu Ala Gln Lys Ile Glu Trp His Glu
1               5                   10                  15

Gly Ser Tyr Arg His Asp Gln His Thr Gly Asp Arg Leu Thr His Pro
            20                  25                  30
```

```
                20                  25                  30
Gln Arg Gln Gln Gln Gly Pro Ser Thr Gly Lys Ile Thr Gly Ile Leu
            35                  40                  45

Phe Gly Leu Thr Gly Ile Thr Leu Val Gly Thr Val Ile Gly Leu Ala
        50                  55                  60

Leu Ala Thr Pro Leu Phe Val Ile Phe Ser Pro Val Ile Val Pro Ala
65                  70                  75                  80

Met Ile Ala Ile Gly Leu Ala Val Thr Gly Phe Leu Thr Ser Gly Thr
                85                  90                  95

Phe Gly Leu Thr Arg Ser Thr Met Ser Val Pro Val Gln Arg Asp Tyr
            100                 105                 110

Val Lys Gly Lys Leu Gln Asp Val Gly Glu Tyr Thr Gly Gln Lys Thr
        115                 120                 125

Lys Asp Leu Gly Gln His His His His His
    130                 135

<210> SEQ ID NO 25
<211> LENGTH: 135
<212> TYPE: PRT
<213> ORGANISM: Artificial Sequence
<220> FEATURE:
<223> OTHER INFORMATION: chemically synthesized

<400> SEQUENCE: 25

Gly Leu Asn Asp Ile Phe Glu Ala Gln Lys Ile Glu Trp His Glu Gly
1               5                   10                  15

Ser Thr Thr Thr Tyr Asp Arg His His Val Thr Thr Thr Gln Pro Gln
                20                  25                  30

Tyr Arg His Asp Gln His Thr Gly Asp Arg Leu Thr His Pro Gln Arg
            35                  40                  45

Gln Gln Gln Gly Pro Ser Thr Gly Lys Ile Met Gly Ile Leu Phe Gly
        50                  55                  60

Leu Thr Gly Ile Thr Leu Val Gly Thr Val Ile Gly Leu Ala Leu Ala
65                  70                  75                  80

Thr Pro Leu Phe Val Ile Phe Ser Pro Val Ile Val Pro Ala Met Ile
                85                  90                  95

Ala Ile Gly Leu Ala Val Thr Gly Phe Leu Thr Ser Gly Thr Phe Gly
            100                 105                 110

Leu Thr Arg Ser Thr Met Ser Val Pro Val Gln Arg Asp Tyr Val Leu
        115                 120                 125

Glu His His His His His His
    130                 135

<210> SEQ ID NO 26
<211> LENGTH: 150
<212> TYPE: PRT
<213> ORGANISM: Artificial Sequence
<220> FEATURE:
<223> OTHER INFORMATION: chemically synthesized

<400> SEQUENCE: 26

Gly Leu Asn Asp Ile Phe Glu Ala Gln Lys Ile Glu Trp His Glu Gly
1               5                   10                  15

Ser Pro Ser Thr Gly Lys Ile Met Gly Ile Leu Phe Gly Leu Thr Gly
                20                  25                  30

Ile Thr Leu Val Gly Thr Val Ile Gly Leu Ala Leu Ala Thr Pro Leu
            35                  40                  45
```

Phe Val Ile Phe Ser Pro Val Ile Val Pro Ala Met Ile Ala Ile Gly
 50                  55                  60

Leu Ala Val Thr Gly Phe Leu Thr Ser Gly Thr Phe Gly Leu Thr Arg
 65                  70                  75                  80

Ser Thr Met Ser Val Pro Val Gln Arg Asp Tyr Val Lys Gly Lys Leu
                 85                  90                  95

Gln Asp Val Gly Glu Tyr Thr Gly Gln Lys Thr Lys Asp Leu Gly Gln
            100                 105                 110

Lys Ile Gln His Thr Ala His Glu Met Gly Asp Gln Gly Gln Gly Gln
        115                 120                 125

Gly Gln Gly Gly Lys Glu Gly Arg Lys Glu Gly Gly Lys Leu Glu
130                 135                 140

His His His His His His
145                 150

<210> SEQ ID NO 27
<211> LENGTH: 132
<212> TYPE: PRT
<213> ORGANISM: Artificial Sequence
<220> FEATURE:
<223> OTHER INFORMATION: chemically synthesized

<400> SEQUENCE: 27

Gly Ser Tyr Arg His Asp Gln His Thr Gly Asp Arg Leu Thr His Pro
1               5                   10                  15

Gln Arg Gln Gln Gln Gly Pro Ser Thr Gly Lys Ile Met Val Ile Met
            20                  25                  30

Ala Leu Leu Pro Ile Thr Gly Ile Leu Phe Gly Leu Ala Gly Ile Thr
        35                  40                  45

Leu Val Gly Thr Val Ile Gly Leu Ala Leu Ala Thr Pro Leu Phe Val
 50                  55                  60

Ile Phe Ser Pro Val Ile Val Pro Ala Met Ile Ala Ile Gly Leu Ala
 65                  70                  75                  80

Val Thr Gly Phe Leu Thr Ser Gly Thr Phe Gly Leu Thr Gly Leu Ser
                 85                  90                  95

Ser Leu Ser Tyr Leu Phe Asn Met Val Arg Arg Ser Thr Met Ser Val
            100                 105                 110

Pro Val Gln Arg Asp Tyr Val Lys Gly Lys Leu Gln Leu Glu His His
        115                 120                 125

His His His His
130

<210> SEQ ID NO 28
<211> LENGTH: 127
<212> TYPE: PRT
<213> ORGANISM: Artificial Sequence
<220> FEATURE:
<223> OTHER INFORMATION: chemically synthesized

<400> SEQUENCE: 28

Gly Ser His Thr Gly Asp Arg Leu Thr His Pro Gln Arg Gln Gln Gln
1               5                   10                  15

Gly Pro Ser Thr Gly Lys Ile Met Val Ile Met Ala Leu Leu Pro Ile
            20                  25                  30

Thr Gly Ile Leu Phe Gly Leu Ala Gly Ile Thr Leu Val Gly Thr Val
        35                  40                  45

Ile Gly Leu Ala Leu Ala Thr Pro Leu Phe Val Ile Phe Ser Pro Val
 50                  55                  60

Ile Val Pro Ala Met Ile Ala Ile Gly Leu Ala Val Thr Gly Phe Leu
65                  70                  75                  80

Thr Ser Gly Thr Phe Gly Leu Thr Gly Leu Ser Ser Leu Ser Tyr Leu
                85                  90                  95

Phe Asn Met Val Arg Arg Ser Thr Met Ser Val Pro Val Gln Arg Asp
            100                 105                 110

Tyr Val Lys Gly Lys Leu Gln Leu Glu His His His His His His
        115                 120                 125

<210> SEQ ID NO 29
<211> LENGTH: 12
<212> TYPE: PRT
<213> ORGANISM: Artificial Sequence
<220> FEATURE:
<223> OTHER INFORMATION: chemically synthesized

<400> SEQUENCE: 29

Pro Val Phe Leu Ile Phe Ser Pro Val Leu Val Pro
1               5                   10

<210> SEQ ID NO 30
<211> LENGTH: 193
<212> TYPE: PRT
<213> ORGANISM: Artificial Sequence
<220> FEATURE:
<223> OTHER INFORMATION: chemically synthesized

<400> SEQUENCE: 30

Met Ala Thr Thr Thr Tyr Asp Arg His His Val Thr Thr Thr Gln Pro
1               5                   10                  15

Gln Tyr Arg His His Asp Gln His Thr Gly Asp Arg Leu Thr His Pro
                20                  25                  30

Gln Arg Gln Gln Gln Gly Pro Ser Thr Gly Lys Ile Met Val Ile Met
            35                  40                  45

Ala Leu Leu Pro Ile Thr Gly Ile Leu Phe Gly Leu Ala Gly Ile Thr
        50                  55                  60

Leu Val Gly Thr Val Ile Gly Leu Ala Leu Ala Thr Pro Leu Phe Val
65                  70                  75                  80

Ile Phe Ser Pro Val Ile Val Pro Ala Met Ile Ala Ile Gly Leu Ala
                85                  90                  95

Val Thr Gly Phe Leu Thr Ser Gly Thr Phe Gly Leu Thr Gly Leu Ser
            100                 105                 110

Ser Leu Ser Tyr Leu Phe Asn Met Val Arg Arg Ser Thr Met Ser Val
        115                 120                 125

Pro Val Gln Arg Asp Tyr Val Lys Gly Lys Leu Gln Asp Val Gly Glu
    130                 135                 140

Tyr Thr Gly Gln Lys Thr Lys Asp Leu Gly Gln Lys Ile Gln His Thr
145                 150                 155                 160

Ala His Glu Met Gly Asp Gln Gly Gln Gln Arg Gly Gly Gly
                165                 170                 175

Lys Glu Gly Arg Lys Glu Gly Gly Lys Leu Glu His His His His
            180                 185                 190

His

VESICLES AND NANOSTRUCTURES FROM RECOMBINANT PROTEINS

CROSS-REFERENCE TO RELATED APPLICATION

The present application is a 35 U.S.C. §371 national phase application of, and claims priority to, International Application No. PCT/US12/21194, filed Jan. 13, 2012, and published under PCT Article 21(2) in English, which claims priority under 35 U.S.C. §119(e) to U.S. Provisional Application No. 61/432,476, filed Jan. 13, 2011, all of which applications are hereby incorporated by reference in their entireties herein.

STATEMENT REGARDING FEDERALLY SPONSORED RESEARCH OR DEVELOPMENT

This invention was made with government support under grant numbers DMR05-20020 awarded by the National Science Foundation and GM081444 awarded by the National Institutes of Health. The government has certain rights in the invention

BACKGROUND OF THE INVENTION

Nanoparticles have attracted interest as potential bioreactors, imaging or diagnostic agents, and vehicles for drug delivery. For these applications, the nanoparticles should ideally be biocompatible, biodegradable, have substantial storage capacity for hydrophilic and hydrophobic solutes, and have tunable properties for targeting cellular structures and releasing solutes on cue (Gindy & Prud'homme, 2009, Exp. Opin. Drug Deliv. 6(8):865-78). Nanoparticles that satisfy some of these constraints include porous particles, metallic or semi-conductor nanoparticles, and vesicles. Of these constructs, vesicles hold particular promise, based on their large storage capacity.

Vesicles consist of a shell of amphiphilic molecules in a tail-to-tail configuration enclosing an aqueous solvent. The canonical structure of vesicle membranes is the bilayer, in which two layers of amphiphiles are ordered such that their hydrophobic tails are oriented inward and their hydrophilic heads are oriented outward toward both the exterior and luminal aqueous phases. Bilayer membranes surround the cells of living organisms, and are selectively permeable, only allowing specific substrates to pass into the cytoplasm.

Vesicles have great potential to be used as flexible delivery systems in vitro and in vivo. In order to be used as therapeutic or diagnostic vehicles, the vesicles may be loaded with hydrophobic or hydrophilic solutes in the membrane or lumen, respectively, and these solutes may be released upon application of specific stimuli (heat, light, or pH, for example). Vesicles could be further designed to present specific targeting moieties on their exterior surface, so that the therapeutic agent contained within the vesicles would be delivered to a specific site (such as a tumor), thereby minimizing collateral toxicity to surrounding tissue. Furthermore, proteins such as proton pumps could be incorporated into the membrane, creating a vesicular bioreactor.

The simplest way to construct a vesicle is from phospholipids and lipid blends (Evans & Needham, 1986, Faraday Disc. Chem. Soc. 81:267-80). Because phospholipids are naturally occurring components, their biocompatibility is not a major concern. Unfortunately, phospholipid vesicles tend to be mechanically weak and unable to withstand the substantial shear stresses in the circulation, and are quickly cleared by the reticulo-endothelial system (Discher et al., 2002, J. Phys. Chem. B 106(11):2848-54). Adding polyethylene glycol chains to the outer lipid shell of phospholipids extends their circulation time, but does not substantially improve their mechanical stability (Lasic & Needham, 1995, Chem. Rev. 95(8):2601-28). Additionally, lipids are rapidly oxidized and difficult to modify chemically, and exist in a narrow range of molecular weights, limiting their use as the main component of tunable vesicles.

Vesicles have been alternatively prepared from synthetic amphiphiles, such as block copolymers (polymersomes) (Discher et al., 1999, Science 284:1143-46) or amphiphilic dendrimers (dendrimerisomes) (Percec et al., 2010, Science 328(5981):1009-14). Like amphiphilic phospholipids, amphiphilic block co-polymers of the correct molecular weight and block fractions self-assemble into a lamellar phase (bilayer) in water (Discher et al., 1999, Science 284: 1143-46). Polymersomes can be made from polymers with a wide variety of molecular weights (Bermudez et al., 2002, Macromol. 35:8203-08) and chemistries (Ahmed & Discher, 2004, J. Contr. Rel. 9(1):37-53; Cheng et al., 2009, Adv. Funct. Mat. 19(23):3753-59; Fraaije et al., 2005, Faraday Disc. 128:355-61; Opsteen et al., 2007, Chem. Comm. 30:3136-38; Upadhyay et al., 2009, Biomacromol. 10(10): 2802-08), and thus their material properties are widely tunable. For example, polymersomes with poly(butadiene) hydrophobic cores may be made mechanically tough by crosslinking the unsaturated side chains in the membrane core (Discher et al., 2002, J. Phys. Chem. B 106(11):2848-54). Alternatively, polymersomes may be stabilized by linking together terminal acrylate groups added to the ends of polymers (Katz et al., 2009, Langmuir 25(8):4429-34). These ultra-tough vesicles are mechanically robust and have long circulation times, and may be used for stable storage of contents such as hemoglobin (for making artificial red blood cells) and imaging agents (Cheng et al., 2009, Adv. Funct. Mat. 19(23):3753-59), and these contents may be released from the vesicles in response to chemical changes (such as pH) or external stimuli (such as light) (Ghoroghchian et al., 2006, Macromol. 39(5):1673-75; Rehor et al., 2003, J. Contr. Rel. 87(1-3):246-47; Kamat et al., 2010, Adv. Funct. Mat. 20:2588-96; Robbins et al., 2009, J. Am. Chem. Soc. 131(11): 3872-74)

However, polymersomes have limitations as vesicle building materials. Polymersomes are made from synthetic polymers, many of which are toxic in humans and animals. They may also be difficult to functionalize with bioactive ligands, resulting in low attachment efficiencies. Furthermore, polymers are typically polydisperse, with wide ranges of molecular weights. The polydispersity limits the precision of the structures that can be assembled from the polymers.

Nanovesicles have also been recently prepared from amphiphilic Janus dendrimers. A dendrimer is a monodisperse branched structure, wherein the number of branches and the chemistry in each branch is tunable. However, one problem in the development of dendrimer-based vesicles is the poor control in attaching ligands to the functional ends of dendrimers, which leads to heterogeneous products. Another problem is the change in polymer phase structure upon attachment of large peptides to the dendrimer. Yet another problem is that dendrimers may include synthetic chemical residues that may be toxic.

As a possible alternative approach, vesicles may be made from peptides or small proteins, which, as naturally occurring molecules, are biocompatible. In theory, proteins may be engineered to have sizes similar to those of vesicle-forming polymers. Furthermore, proteins may be engineered with exquisitely fine control (to avoid the polydispersity of polymers) and chemical diversity (using the library of naturally occurring amino acids). Specific functional groups may be genetically introduced in the peptide chain by changing the gene that codes for the protein, or may be attached by protein-ligation methods to protein molecules in the preformed vesicle.

As an example of vesicles prepared with proteins, a pH switchable vesicle was prepared from a di-block co-peptide of poly-(L-glutamic acid)-b-poly(L-lysine), $E_{15}K_{15}$ (Rodriguez-Hernandez & Lecommandoux, 2005, J. Am. Chem. Soc. 127(7):2026-27). At pH values between 5 and 9, both amino acid chains were charged, and the peptide chains were dispersed. However, at pH values below 5 or above 9, one of the two chains was neutralized, the other chain remained charged, and the peptide assembled into vesicles with an orientation dictated by pH (Deming, 2007, Prog. Pol. Sci. 32(8-9):858-75; Holowka et al., 2007, Nature Mat. 6(1):52-57; Holowka & Deming, 2010, Macromol. Biosci. 10(5):496-502; Holowka et al., 2005, J. Am. Chem. Soc. 127(35):12423-28). Likewise, poly-(L-lysine)-b-poly(L-leucine) di-block co-peptide polymers ($K_nL_m$) were synthesized, and $K_{60}L_{20}$ was shown to assemble into vesicular membranes. Peptides with other ratios of the two amino acids assembled into structures different from vesicles, such as fibrils and sheet-like membranes. Moreover, vesicles of $K_{60}L_{20}$ could be extruded through polycarbonate membranes into 100 nm vesicles, useful for biological applications (Holowka et al., 2005, J. Am. Chem. Soc. 127(35):12423-28). Vesicles from poly(L-arginine)-b-poly(L-leucine) in the same molar ratio ($R_{60}L_{20}$) were found to be internalized by HeLa cells in culture (Holowka et al., 2007, Nature Mat. 6(1):52-57). In this aspect, the peptide $R_{60}L_{20}$ mimicked TAT peptides, which are rich in arginine residues and facilitate cell internalization.

Taken together, these results demonstrate that polypeptide chains may be used to prepare vesicles, and the incorporation of specific amino acids in the peptide chain may allow control of biological activity and function of the formed vesicle structures. However, the use of peptides as building blocks of vesicles still faces challenges. Such peptides have so far been prepared by synthetic chemical methods, rather than by molecular biology, and are thus polydisperse. Chemical ligation of functional groups to the peptide terminals is often inefficient, leading to complex mixtures. Furthermore, chemical methods allow the synthesis of peptides of only moderate size, whereas yields and purities are often poor for larger target peptides.

Oleosins are plant proteins that solubilize fat bodies in plants. Oleosins have an N-terminal hydrophilic segment, followed by a hydrophobic core and another hydrophilic segment at the C-terminus (Lacey et al., 1998, Biochem. J. 334: 469-77; Hsieh & Huang, 2004, Plant Physiol. 136(3):3427-34). The hydrophobic core is more conserved than the N- and C-terminal domains, which are thought to interact with the surface of oil bodies (Alexander et al., 2002, Planta 214(4): 546-51; Beaudoin & Napier, 2002, Planta 215(2):293-303). Modeling studies suggested that the hydrophobic core is helical (possibly a coiled-coil) and bifurcated by a proline knot (a highly conserved stretch containing three prolines that introduces a 180° turn in the chain) (Alexander et al., 2002, Planta 214(4):546-51).

Oleosin enters the endoplasmic reticulum (ER) co-translationally, where it is introduced into the wall of a growing oil body (Beaudoin & Napier, 2000, Planta 210(3):439-45). The hydrophobic core of oleosin appears to be essential to anchoring the nascent protein in the ER; substituting leucines for the three prolines leaves the protein able to enter the ER, but unable to transfer to the oil body (Abell et al., 1997, Plant Cell 9(8):1481-93). Replacing half of the hydrophobic core of oleosin with a duplicate of the other half appears to have no effect on the ability of the protein to insert into the ER (Abell et al., 2004, Plant J. 37(4):461-70). This suggests that the degree of hydrophobicity and the length of the hydrophobic core (rather than its specific sequence) give oleosin its unique geometry in membranes. In the case of the sesame oleosin, reducing the size of the hydrophobic core by half had no effect on the ability of oleosin to stabilize artificial oil bodies (Peng et al., 2007, J. Agr. Food Chem. 55(14):5604-10). The ability of oleosins to stabilize oil bodies is also not affected by protein fusion at the termini of the protein chain (Chiang et al., 2007, Prot. Expr. Pur. 52(1):14-18). These observations have resulted in attempts to target the expression of clinically important proteins in plants to oil bodies where they may be easily harvested (Chiang et al., 2007, Prot. Expr. Pur. 52(1): 14-18; Chiang et al., 2005, J. Agric. Food Chem. 53(12): 4799-4804; Nykiforuk et al., 2006, Plant Biotech. J. 4(1):77-85). Oleosin fusions have also been used for protein purification in vitro (Chiang et al., 2007, Prot. Expr. Pur. 52(1):14-18).

There remains a need in the art to identify novel chemical compounds or biomolecules that may be utilized to generate vesicles useful for drug delivery or imaging techniques. The ideal chemical compound or biomolecule that forms the vesicles should be easily prepared and isolated, biocompatible, mechanically robust, and responsive to environmental conditions. The present invention fulfills these needs.

BRIEF SUMMARY OF THE INVENTION

The invention includes a composition comprising a protein comprising a sequence that has at least 80% homology to an oleosin-like protein selected from the group consisting of SEQ ID NOs:1-3, SEQ ID NOs:13-28, and combinations thereof.

In one embodiment, the sequence has at least 90% homology to an oleosin-like protein selected from the group consisting of SEQ ID NOs:1-3, SEQ ID NOs:13-28, and combinations thereof. In another embodiment, the sequence has at least 95% homology to an oleosin-like protein selected from the group consisting of SEQ ID NOs:1-3, SEQ ID NOs:13-28, and combinations thereof.

In one embodiment, a receptor binding motif is attached to the N-terminus or the C-terminus of the sequence via an amide bond. In another embodiment, the motif is selected from the group consisting of SEQ ID NOs:4-6. In yet another embodiment, the hydrophobic segment of the oleosin-like protein is replaced with a hydrophobic elastin-like protein or a leucine zipper. In yet another embodiment, the proline knot of the oleosin-like protein is replaced with at least one repeat of SEQ ID NO:7. In yet another embodiment, at least two residues of the oleosin-like protein are replaced with cysteine residues. In yet another embodiment, at least one tyrosine residue in the oleosin-like protein is converted to a L-DOPA residue via a chemical reaction. In yet another embodiment, at least two of the L-DOPA residues are further crosslinked via a chemical reaction. In yet another embodiment, at least one residue in the proline knot of the oleosin-like protein is replaced with a tyrosine residue. In another embodiment, at least one sequence selected from the group consisting of SEQ ID NOs:8-12 is inserted in the oleosin-like protein (i) at the junction of hydrophilic and hydrophobic segments, or (ii) within the hydrophilic segment.

The invention also includes a composition comprising a vesicle, wherein the vesicle comprises a protein comprising a sequence that has at least 80% homology to an oleosin-like protein selected from the group consisting of SEQ ID NOs: 1-3, SEQ ID NOs:13-28, and combinations thereof.

In one embodiment, the composition further comprises a compound encapsulated within the vesicle, wherein the compound is selected from the group consisting of a gas, drug, fluorescent dye, radioactive probe, salt, protein, and nucleic acid. In another embodiment, the composition further comprises at least one pharmaceutically acceptable carrier.

The invention also includes a method of preparing a vesicle. The method comprises providing a composition comprising a protein comprising a sequence that has at least 80% homology to an oleosin-like protein selected from the group consisting of SEQ ID NOs:1-3, SEQ ID NOs:13-28, and combinations thereof. The method further comprises suspending the composition in an organic solvent, to generate a first system. The method further comprises optionally adding a compound to the first system. The method further comprises removing at least part of the organic solvent from the first system, to form a second system. The method further comprises suspending the second system in an aqueous solvent, to form a third system. The method further comprises optionally adding the compound to the third system. The method further comprises homogenizing the third system, whereby the vesicle is generated, wherein the compound is encapsulated within the vesicle.

The invention also includes a method of delivering a compound to a subject in need thereof, wherein the compound is encapsulated within a vesicle. The method comprises administering to the subject a pharmaceutical composition comprising a pharmaceutically effective amount of the vesicle, wherein the vesicle comprises a protein comprising a sequence that has at least 80% homology to an oleosin-like protein selected from the group consisting of SEQ ID NOs: 1-3, SEQ ID NOs:13-28, and combinations thereof.

In one embodiment, the compound is selected from the group consisting of a gas, drug, fluorescent dye, radioactive probe, salt, protein, and nucleic acid. In another embodiment, the subject is a mammal. In yet another embodiment, the mammal is human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising As illustrated in FIG. 1A, sunflower oleosin is a protein with terminal hydrophilic residues and a hydrophobic stalk and hairpin (proline knot corresponds to SEQ ID NO:29). As illustrated in FIG. 1B, oleosin solubilizes triacylglycerol with the help of phospholipids in an oil body structure. FIG. 1C illustrates a truncated amino acid sequence of sunflower oleosin (SEQ ID NO:30), with the hydrophobic core doubly underlined, the proline knot shown in a box, and a portion of the hydrophilic section singly underlined. A ribbon model of the hydrophobic central core is illustrated at the bottom. Dotted lines show hydrogen-bonding interactions to side-chains.

FIG. 2 illustrates protein sequences for engineered oleosin-like proteins. The oleosin-hydrophobic protein (oleosin-2) (SEQ ID NO:2) is about 55% hydrophobic, and the oleosin-hydrophilic protein (oleosin-3) (SEQ ID NO:3) is about 62% hydrophilic. Hydrophilic blocks are doubly underlined, and hydrophobic blocks are singly underlined. Both oleosin-like proteins retain the proline knot in the hydrophobic domain, and a 6-His tag has been added to enable purification.

FIG. 3, comprising FIGS. 3A-3C, illustrates SDS-PAGE and Western blot of recombinant oleosin-like proteins overexpressed in $E.$ $Coli$. The oleosin-hydrophilic and oleosin-hydrophobic proteins have expected molecular weights at 18.3 kDa (FIG. 3A) and 17.1 kDa (FIG. 3B), respectively. A separate gel was transferred onto a nitrocellulose membrane and was subjected to an immunoassay using antibodies against the six-histidine tag (FIG. 3C). SDS-PAGE and Western blotting showed multimers of the oleosin-like proteins in the purified solution FIG. 4 illustrates the structure of oleosin-like proteins. Oleosin-like proteins (left) may orient in a block-like structure in the bilayer membrane. Since the proline loop is retained in the oleosin-like protein, the molecule likely retains its loop. The bilayer vesicles (right) have a hydrophobic membrane core and a hydrophilic lumen created by the self-assembly of the protein.

FIG. 6, comprising FIGS. 6A-6D, illustrates confocal (FIGS. 6A & 6C) and differential interference contrast (DIC) (FIGS. 6B & 6D) images of giant bilayer protein vesicles with Nile Red encapsulated in the membrane. FIGS. 6A & 6B illustrate oleosin-hydrophilic vesicles, and FIGS. 6C & 6D illustrate oleosin-hydrophobic vesicles. All scale bars are 10 p.m.

FIG. 7, comprising FIGS. 7A-7C, is a series of schematic drawings of oleosin proteins and predicted vesicle structure. The proteins have been split into three sections. N and C are the hydrophilic arms and H is the hydrophobic core. Numbers represent the number of amino acids in each block. FIG. 7A: Oleo-WT; N=42, H=87, C=57. FIG. 7B: Oleo-M1; N=17, H=65, C=17. FIG. 7C: schematic of oleosin bilayer vesicle. Each protein has a conserved proline knot bifurcating the hydrophobic block (H) consisting of 12 total amino acids.

FIG. 8, comprising FIGS. 8A-8C, illustrates analysis of oleosin proteins. FIG. 8A: SDS-PAGE gel illustrating protein purity for various organic solutions. Lanes: 1) protein marker. Lanes 2-6 are Oleo-WT and lanes 7-11 are Oleo-M1. The lane orders are: 10:0:0, 1:0:9, 1:1:8, 1:3:6, 1:5:4 for both sets (200 mM $Na_2CO_3$:chloroform:methanol) (v/v/v). FIG. 8B: MALDI spectra of Oleo-WT. Peak: 20581. FIG. 8C: MALDI spectra of Oleo-M1. Peak: 13128.

FIG. 9, comprising FIGS. 9A-9B, illustrates secondary structure analysis of oleosin proteins. FIG. 9A: Far UV spectra of various mutant protein molecules in 50% TFE. Data was fit using the CDSSTR program with SMP180 reference dataset in DichroWeb software. FIG. 9B: Estimation of secondary structure based on fits in FIG. 9A.

FIG. 10, comprising FIGS. 10A-10C, illustrates self-assembled structures formed in aqueous solutions from oleo-M1. Cryo-TEM images showing (FIG. 10A) vesicles, and (FIG. 10B) tubular structures (scale bars are 200 nm). FIG. 10C: Dynamic light scattering showing peaks for vesicles and worms after 1:1:8 (200 mM $Na_2CO_3$:chloroform:methanol) (v/v/v) injections.

FIG. 11, comprising FIGS. 11A & 11D: DIC. FIGS. 11B & 11E: Nile Red fluorescence. FIGS. 11C & 11F: Calcein fluorescence. All scale bars are 10 µm.

FIG. 12, comprising FIG. 12A: SDS-PAGE showing protein purity for various oleosin mutants. Expected molecular weights (kDa): Oleo-WT (20.8), 7-87-57 (18.5), 7-87-7 (13.2), 27-65-27 (15.1), and Oleo-M1 (13.1). FIG. 12B: Table showing proteins purified and expressed to date with expected molecular weight (Da) and estimated pI.

FIG. 14, comprising FIGS. 14A-14C, is a series of cryo-TEM images illustrating changes in geometric packing behavior for the oleosin mutants, based on geometric changes in the protein. Figure A: 12-65-12 formed sheets when injected into deionized water. FIG. 14B: Increasing the head group size shifted the macromolecular structure from sheets to vesicles as seen in 17-65-17. FIG. 14C: Additional increases in head group size showed the formation of worm-like micelles as seen in 27-65-27.

DETAILED DESCRIPTION OF THE INVENTION

Figure 1A:
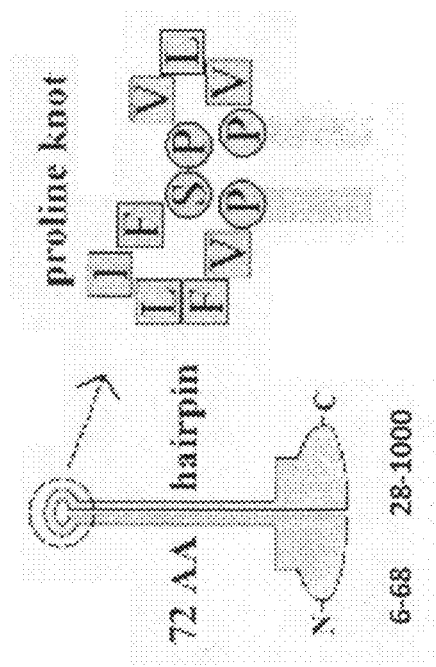
FIGS. 1A-1C, illustrates the structure of oleosin (adapted from Alexander et al., 2002, Planta 214 (4):546-51 and Huang, 1992, Annu. Rev. Plant Physiol., Plant Mol. Biol. 43:177-20).
Figure 1B:
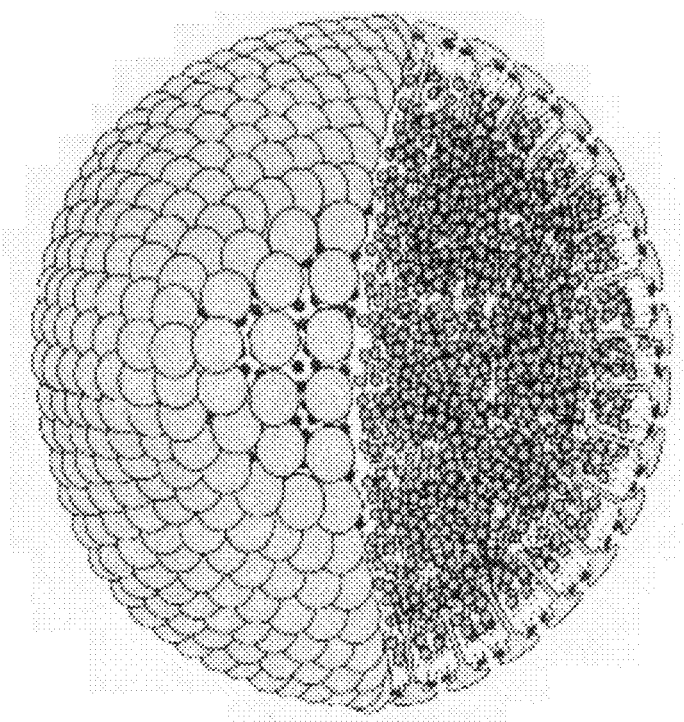
Figure 1C:
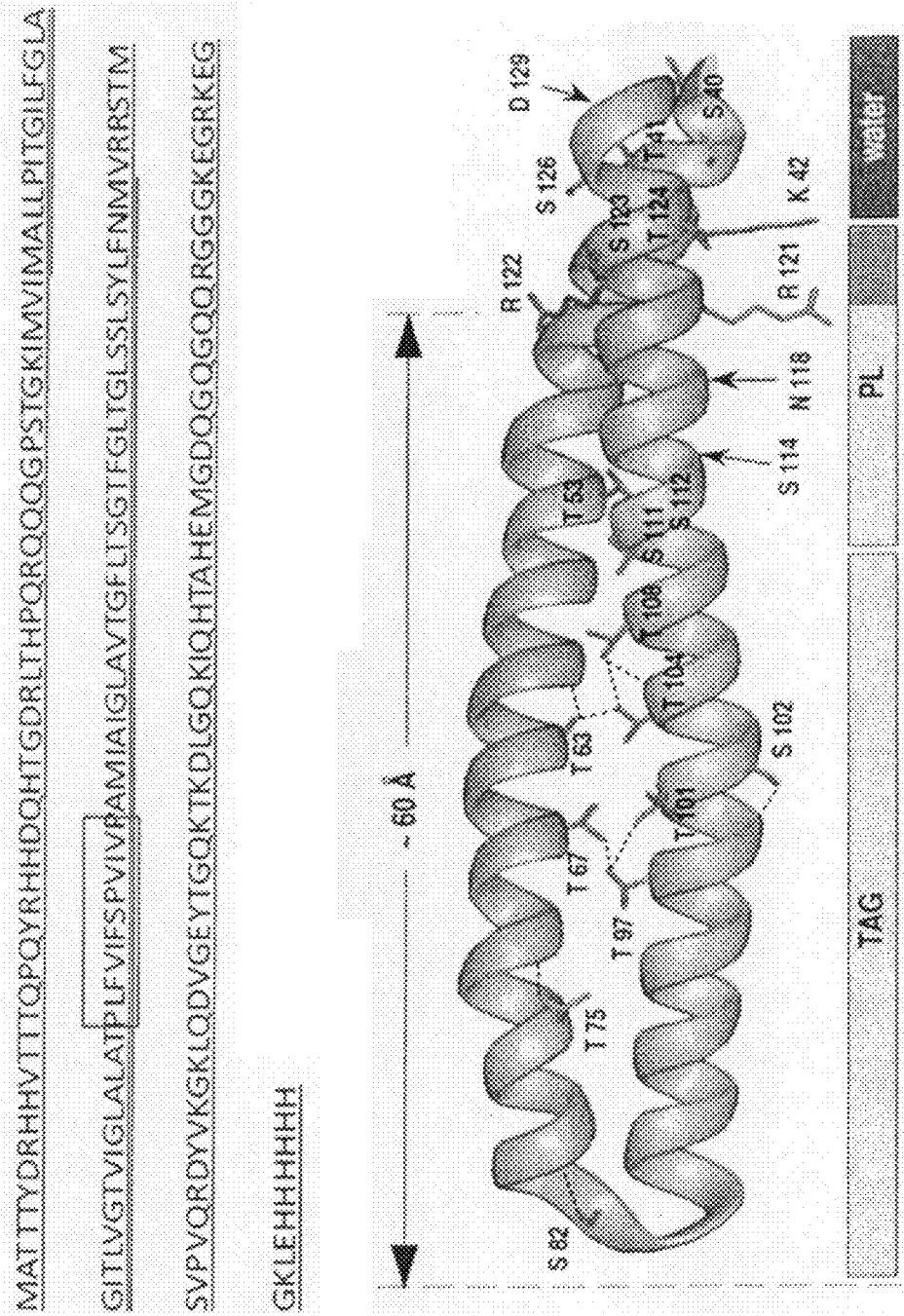

The present invention relates to the discovery that vesicles may be prepared from oleosin-like proteins, which are prepared by molecular biology methods. This discovery is unexpected in view of the prior art, wherein no stable and biocompatible vesicles have been prepared from recombinantly made proteins only. Molecular biology and/or chemical ligation tools may be utilized to prepare recombinantly made protein, with a carefully controlled display of chemical functionality on the peptide backbone, which may then be assembled into a vesicle. The biocompatibility of protein-based vesicles represents a significant advance over the properties of polymer-based synthetic vesicles. The invention described herein indeed represents a novel paradigm for making vesicles from biocompatible components.

In one aspect, the vesicles of the present invention are biocompatible, because they are made from purely biological components. In another aspect, biofunctionality can be directly incorporated into the peptide chain using molecular biology tools or chemical ligation reactions. In yet another aspect, strategies for the dynamic responsiveness of proteins, such as changes in solubility due to protonation-deprotonation, or changes in helical or secondary structure induced by binding of cations, may be used to control the structure of the vesicle. These characteristics represent advances of protein-based vesicles over synthetic membranes made from polymers or dendrimers. The proteins described herein are single molecules of defined molecular weight, and the vesicles prepared with these proteins are uniform and easily tunable. The compositions and methods of the present invention thus allow the promise of protein-based vesicles to reach its full potential. In one aspect, the proteins of the invention represent a substantial advance over the polypeptide vesicles, because the amino acid sequence is fully adjustable, and not restricted to blocks of identical amino acids.

In another aspect, the ability to assemble vesicles from proteins made by molecular biology achieves the characteristics of an ideal vesicular carrier: biocompatible, mechanically robust, responsive to environmental conditions so that they can release their contents on cue, and can be targeted to specific receptors on target cells. Designer functionality may be easily incorporated into the peptide backbone or to the peptide terminus and hence conveyed to the vesicle. Furthermore, the proteins are monodisperse, which also allows *facile* self-assembly and structural design at the nanoscale. Overall, the invention represents a novel paradigm for making vesicles out of biocompatible components.

In one aspect, the present invention allows for the assembly of vesicles from recombinantly made protein where designer functionality may be easily swapped into the peptide backbone and conveyed directly to the vesicle. The biocompatibility of the materials represents a significant advance over synthetic vesicles made from polymers. The ability to make monodisperse proteins with embedded segments of designed sequence by molecular biology is a significant advance over current methods of assembling vesicles from polymerized polydisperse block copolypeptides.

In one embodiment, vesicles are prepared from recombinant oleosin and characterized. Mutant genes of the protein oleosin are prepared, these genes are expressed and purified, and the resulting protein is characterized and assembled into vesicles. Protein purity is characterized through SDS-PAGE analysis and mass spectroscopy. The secondary structure of each protein is measured using circular dichroism (CD) to understand how the truncations affect the structure of the folded protein, and how structure affects vesicle assembly. Multiple self-assembly procedures are explored to test vesicle formation. Self-assembly is monitored by confocal microscopy and cryo-transmission electron microscopy (cryo-TEM).

In another embodiment, vesicle formation is optimized and stabilized by controlling protein properties through specific modifications. Changing the overall geometry of the protein to find the optimal protein for vesicle formation increases the stability and yield of the vesicles. A library of oleosin mutants is prepared to test various factors relating to self-assembly. For proteins that assemble into vesicles, the material properties of the membrane may be altered using: 1) Specific point mutations in the protein backbone or 2) Addition of cysteine residues. To create membranes with more fluid-like character, hydrogen bond forming amino acids are removed from the hydrophobic block and replaced with bulky hydrophobic amino acids. Conveniently, oleosin contains no cysteine residues. Cysteine residues are introduced though point mutations throughout the hydrophilic arms, and the resulting oleosin vesicles are crosslinked through formation of disulfide bonds. The material strength of the resulting vesicles is measured using micropipette aspiration.

In yet another embodiment, protein vesicles are functionalized through molecular biology. A major advantage of protein vesicles is the ease of functionalization through molecular biology, such as 1) Adding specific peptide motifs to oleosin terminus for cell specific targeting or 2) Introducing protease cleavable domains to the protein backbone, and measuring release from protease-cleavable vesicles. Integrin binding peptides (such as RGDS and PHSRN) and a TAT peptide are attached to direct the specific binding and internalization of oleosin vesicles into cultured human umbilical vein endothelial cells (HUVECs), and the relative efficiency of cell binding and entry is measured in comparison to vesicles lacking modification. Proteases recognize specific short peptide sequences. Using molecular biology, these sequences are introduced at random to both hydrophilic arms, and the release of stored contents from vesicles is measured after addition of proteases. The experiments determine the most efficient location for placing protease cleavable domains for optimal release for biological applications.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to utilize the disclosed compositions or perform the disclosed methods.

As used herein, the term "CD" refers to circular dichroism.

As used herein, the term "HUVEC" refers to human umbilical vein endothelial cell.

As used herein, the term "cryo-TEM" refers to cryo-transmission electron microscopy.

As used herein, the term "LSCM" refers to laser scanning confocal microscopy.

As used herein, the term "ELP" refers to elastin-like peptides.

As used here, the terms "Oleosin-1" or "Oleo-WT" refers to SEQ ID NO:1.

As used herein, the term "Oleosin-2" or "oleosin-hydrophobic" or "25-87-40" refers to the peptide of SEQ ID NO:2 or a salt thereof.

As used herein, the term "Oleosin-3" or "oleosin-hydrophilic" or "42-65-57" refers to the peptide of SEQ ID NO:3 or a salt thereof.

As used herein, the term "7-87-7" refers to the peptide of SEQ ID NO:13 or a salt thereof.

As used herein, the term "7-87-57" refers to the peptide of SEQ ID NO:14 or a salt thereof.

As used herein, the term "42-87-7" refers to the peptide of SEQ ID NO:15 or a salt thereof.

As used herein, the term "12-87-27" refers to the peptide of SEQ ID NO:16 or a salt thereof.

As used herein, the term "7-87-12" refers to the peptide of SEQ ID NO:17 or a salt thereof.

As used herein, the term "12-87-12" refers to the peptide of SEQ ID NO:18 or a salt thereof.

As used herein, the term "22-87-37" refers to the peptide of SEQ ID NO:19 or a salt thereof.

As used herein, the term "42-87-32" refers to the peptide of SEQ ID NO:20 or a salt thereof.

As used herein, the term "7-65-7" refers to the peptide of SEQ ID NO:21 or a salt thereof.

As used herein, the term "12-65-12" refers to the peptide of SEQ ID NO:22 or a salt thereof.

As used herein, the term "Oleosin mutant 1" or "Oleo-M1" refers to the peptide of SEQ ID NO:23 or a salt thereof.

As used herein, the term "27-65-27" refers to the peptide of SEQ ID NO:24 or a salt thereof.

As used herein, the term "42-65-7" refers to the peptide of SEQ ID NO:25 or a salt thereof.

As used herein, the term "7-65-57" refers to the peptide of SEQ ID NO:26 or a salt thereof.

As used herein, the term "27-87-12" refers to the peptide of SEQ ID NO:27 or a salt thereof.

As used herein, the term "22-87-12" refers to the peptide of SEQ ID NO:28 or a salt thereof.

As used herein, the terms "protein" or "truncated protein" are used interchangeably, and refer to a compound comprised of amino acid residues covalently linked by peptide bonds. In one aspect, the terms "protein," "peptide" and "polypeptide" may be used interchangeably. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, variants of proteins, modified proteins, derivatives, analogs, and fusion proteins, among others. The proteins include natural proteins, recombinant proteins, synthetic proteins, or a combination thereof. A protein may be a receptor or a non-receptor.

As used herein, amino acids are represented by the full name thereof, by the three-letter code, as well as the one-letter code corresponding thereto, as indicated in the following table. The structure of amino acids and their abbreviations can also be found in the chemical literature, such as in Stryer, 1988, "Biochemistry", 3$^{rd}$ Ed., W. H. Freeman and Co., New York.

| Full Name | Three-Letter Code | One-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "fragment," as applied to a protein or peptide, refers to a subsequence of a larger protein or peptide. A "fragment" of a protein or peptide may be at least about 10 amino acids in length; for example, at least about 50 amino acids in length; more preferably, at least about 100 amino acids in length; even more preferably, at least about 200 amino acids in length; particularly preferably, at least about 300 amino acids in length; and most preferably, at least about 400 amino acids in length.

As used herein, a "nucleic acid" refers to a polynucleotide and includes polyribonucleotides and polydeoxyribonucleotides.

As used herein, the term "homologous" refers to the subunit sequence similarity between two polymeric molecules, e.g., between two nucleic acid molecules, such as two DNA molecules or two RNA molecules, or between two protein molecules. When a subunit position in both of the two molecules is occupied by the same monomeric subunit; e.g., if a position in each of two DNA molecules is occupied by adenine, they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 3'-ATTGCC-5' and 3'-TATGGC-5' are 50% homologous. As used herein, "homology" is used synonymously with "identity."

As used herein, the term "substantially the same" amino acid sequence is defined as a sequence with at least 70%, preferably at least about 80%, more preferably at least about 90%, even more preferably at least about 95%, and most preferably at least 99% homology to another amino acid sequence, as determined by the FASTA search method in accordance with Pearson & Lipman, Proc. Natl. Inst. Acad. Sci. USA 1988, 85:2444-2448.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the terms "effective amount" and "pharmaceutically effective amount" refer to a nontoxic but sufficient amount of an agent or drug to provide the desired biological result. That result can be reduction and/or alleviation of the signs, symptoms, or causes of a disease or disorder, imaging or monitoring of an in vitro or in vivo system (including a living organism), or any other desired alteration of a biological system. An appropriate effective amount in any individual case may be determined by one of ordinary skill in the art using routine experimentation.

An "individual" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

"Isolated" means altered or removed from the natural state through the actions of a human being. For example, a nucleic acid or a protein naturally present in a living animal is not "isolated," but the same nucleic acid or protein partially or completely separated from the coexisting materials of its natural state is "isolated." An isolated nucleic acid or protein can exist in substantially purified form, or can exist in a non-native environment such as, for example, a host cell.

By the term "specifically bind" or "specifically binds," as used herein, is meant that a first molecule (e.g., an antibody) preferentially binds to a second molecule (e.g., a particular antigenic epitope), but does not necessarily bind only to that second molecule.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions of the Invention

The invention includes a composition comprising a protein or truncated protein that comprises a sequence having at least 80% homology to an oleosin-like protein selected from the group consisting of SEQ ID NOs:1-3, SEQ ID NOs:13-28, and combinations thereof.

In one embodiment, the sequence has at least 90% homology to an oleosin-like protein selected from the group consisting of SEQ ID NOs:1-3, SEQ ID NOs:13-28, and combinations thereof. In another embodiment, the sequence has at least 95% homology to an oleosin-like protein selected from the group consisting of SEQ ID NOs:1-3, SEQ ID NOs:13-28, and combinations thereof. In yet another embodiment, the sequence is selected from the group consisting of SEQ ID NOs:1-3, SEQ ID NOs:13-28, and combinations thereof.

In one embodiment, a receptor binding motif is attached to the N-terminus or the C-terminus of the sequence via an amide bond. In another embodiment, the motif is selected from the group consisting of SEQ ID NOs:4-6.

In one embodiment, the hydrophobic segment of the oleosin-like protein is replaced with a hydrophobic elastin-like protein or a leucine zipper. In yet another embodiment, the proline knot of the oleosin-like protein is replaced with at least one repeat of SEQ ID NO:7. In yet another embodiment, at least one residue in the proline knot of the oleosin-like protein is replaced with a tyrosine residue.

In one embodiment, at least two residues of the oleosin-like protein are replaced with cysteine residues. In another embodiment, at least one tyrosine residue in the oleosin-like protein is converted to a L-DOPA residue via a chemical reaction. In yet another embodiment, at least two of the L-DOPA residues are further crosslinked via a chemical reaction.

In one embodiment, at least one sequence selected from the group consisting of SEQ ID NOs:8-12 is inserted in the oleosin-like protein (i) at the junction of hydrophilic and hydrophobic segments, or (ii) within the hydrophilic segment.

The invention also includes a composition comprising a vesicle. The vesicle comprises a protein comprising a sequence that has at least 80% homology to an oleosin-like protein selected from the group consisting of SEQ ID NOs: 1-3, SEQ ID NOs:13-28, and combinations thereof.

In one embodiment, the composition further comprises a compound encapsulated within the vesicle, wherein the compound is selected from the group consisting of a gas, drug, fluorescent dye, radioactive probe, salt, protein, and nucleic acid. In another embodiment, the composition further comprises at least one pharmaceutically acceptable carrier.

Methods of the Invention

The invention includes a method of preparing a vesicle. The method comprises the step of providing a composition comprising a protein comprising a sequence that has at least 80% homology to an oleosin-like protein selected from the group consisting of SEQ ID NOs:1-3, SEQ ID NOs:13-28, and combinations thereof. The method further comprises the step of suspending the composition in an organic solvent, to generate a first system. The method further comprises the optional step of adding a compound to the first system. The method further comprises the step of removing at least part of the organic solvent from the first system, to form a second system. The method further comprises the step of suspending the second system in an aqueous solvent, to form a third system. The method further comprises the optional step of adding the compound to the third system. The method further comprises the step of homogenizing the third system, to generate the vesicle, wherein the compound is encapsulated within the vesicle.

The invention also includes a method of delivering a compound to a subject in need thereof, wherein the compound is encapsulated within a vesicle, comprising the step of administering to the subject a pharmaceutical composition comprising a pharmaceutically effective amount of the vesicle, wherein the vesicle comprises a protein comprising a sequence that has at least 80% homology to an oleosin-like protein selected from the group consisting of SEQ ID NOs: 1-3, SEQ ID NOs:13-28, and combinations thereof.

In one embodiment, the compound is selected from the group consisting of a gas, drug, fluorescent dye, radioactive probe, salt, protein, and nucleic acid. In another embodiment, the subject is a mammal. In yet another embodiment, the mammal is human.

Preparation and Characterization of Vesicles with Recombinant Oleosin

The ability to create and express oleosin mutant genes and purify and characterize the resulting protein is assessed prior to vesicle formation. After expression and purification is analyzed, the protein can be tested for self-assembly. The manner in which truncations or alterations in the structure of oleosin affect the ability to assemble into membranes is assessed by cryo-TEM, dynamic light scattering (DLS), and confocal microscopy. In one embodiment, this analysis sets the foundation for work on vesicle stability, membrane stiffness, and vesicle functionalization.

The ability to create oleosin genes, express these genes, and purify and characterize the resulting proteins is assessed. Expression and purity of the protein is assessed through SDS-PAGE electrophoresis and mass spectroscopy. The protein secondary structure may also affect the formation of bilayer membranes. The overall secondary structure for each variation created is measured through circular dichroism and cataloged. This allows a better understanding of the oleosin structure as well as the relationship between secondary structure and self-assembly.

Oleosin is a hairpin molecule with two hydrophilic arms. Oleosin may be mutated with: a) serial truncations of the either the N-terminal or C-terminal hydrophilic blocks or b) reduction of the hydrophobic chains, to test the importance of hydrophobic sequence on membrane formation. Expression of each mutant is tested and distinct purification techniques are used to find the optimal yield and purity. The self-assembly of the protein is tested using standard polymer techniques such as solvent injection, thin film rehydration, and sonication. Structural determination is corroborated at the nanoscale through dynamic light scattering (DLS) and cryo-TEM imaging. Micron sized vesicles are imaged using confocal microscopy.

Optimizing Vesicle Formation and Stability by Controlling Protein Properties Through Specific Modifications The membrane properties of protein vesicles may be systematically changed through molecular biology. The ability to form vesicles may depend on three parameters—the isoelectric point of the protein, the hydrophilic block fraction, and the total molecular weight of the protein. Additional process parameters such as concentration and volume fraction of the injection may also be explored. The protein molecules must retain a certain geometry to pack into a vesicular membrane. When an optimal protein is created, specific amino acids may be systematically altered to change the membrane properties. Controlling the membrane properties provide the ability to release or retain molecules encapsulated inside the vesicle allowing for a wide range of applications.

The material properties of the resulting vesicles may be measured using micropipette aspiration, which has been extensively used to measure the rheology of polymersomes and dendrimersomes. The area expansion modulus ($K_a$) and the critical areal strain before failure for each giant vesicle are measured.

Stabilization of Vesicles Through Protein Geometry:

A library of proteins with various isoelectric points, molecular weights, and hydrophilic fractions is created, and solvent injection is used to create giant protein vesicles. The vesicle stability is monitored visually with confocal microscopy over time. Additionally, a library of proteins is created using bottom-up design using oleosin as a reference molecule. For instance, the hydrophobic block could be replaced with a block that tapers in size of the exposed side groups to allow for better membrane packing. Optimized protein molecules are selected based on expression yield, vesicle yield, and vesicle stability.

Softening Vesicles:

The ability to change the mechanical properties by altering the hydrophobic block of the protein is demonstrated. The hydrophobic block contains multiple amino acid side chains, such as threonine, which are capable of forming hydrogen bonds with neighboring protein molecules. Through point mutations, hydrogen bond forming amino acids are replaced with bulky aromatic amino acids to decrease the cohesive interaction between protein molecules in the membrane. The vesicle is expected to become more fluid (exhibit a smaller area expansion modulus) as the cohesive interactions between protein chains are decreased.

Stiffening Vesicles:

Sunflower oleosin has no cysteines. At least two cysteines are needed per molecule to effect continuous cross-linking. Polyoleosins have been shown to confer enhanced stability to oil bodies, when compared to monomeric oleosins. Thus cross-linking locally may be an effective strategy to make stiffer materials. The location of the cysteines is of importance in minimize intramolecular crosslinks in favor of intermolecular links. A library of oleosins with multiple cysteines is prepared, to determine optimal cysteine locations for extended cross-linking. The extent of cross-linking may be varied through adjusting the number of cysteine residues in each chain. Cross-linking is achieved through oxidants such as oxidized glutathione or ferricyanide. The ability to widely tune the material strength of vesicles enables oleosin vesicles to be used for a wide spectrum of applications, from stable storage (encapsulation of imaging agents) to *facile* release (for drug delivery).

Functionalization of Protein Vesicles Through Molecular Biology

In terms of oleosin-based vesicles, one may incorporate functionality into the protein backbone, and directly express and assemble the biofunctionality into membrane structures. This may be shown in two ways: 1) The addition of receptor-binding motifs to the terminal ends of oleosin, and 2) Introducing protease cleavable domains into the protein backbone. Vesicles may be assembled with a variety of cell-binding motifs and cell internalization may be tested. Every molecule is modified with the desired peptide, eliminating the difficult chemistry and polydispersity seen in polymer and lipid systems. This provides a simple and reliable method to specifically target protein vesicles to cell and induce binding and/or internalization.

Proteases are enzymes that target peptide motifs of specific sequences. Microorganisms use specific proteases to gain infection, endothelial cells employ proteases to activate surface receptors, and proteases cleave ingested proteins in the endosomal pathway. Extensive online databases of protease activity have been established. Degradation of specific protein arms by proteases, which reduces the size of the hydrophilic blocks, may cause vesicle degradation. Clearly, cleavage at the junction between hydrophilic and hydrophobic domains would lead to vesicle destabilization. However, such protease cleavable domains might be inaccessible to proteases. Thus, the location of protease domains necessary to induce vesicle failure is investigated.

Addition of Peptide Binding Motifs:

Nucleotide stretches coding for the peptides of interest (the integrin receptor binding peptides RGDS (SEQ ID NO:4), PHSRN (SEQ ID NO:5), and a TAT peptide for cell penetration, RKKRRQRRR (SEQ ID NO:6)) are appended to the N-terminus or C-terminus of an optimized oleosin (see elsewhere herein) using standard molecular biology techniques. The ability of expressed oleosins containing these motifs to make vesicles is assessed. If these molecules do not make vesicles themselves, they may be mixed with different ratios of any of the oleosins assembled as described elsewhere herein, and the degree of cell binding and penetration is measured as a function of the percentage of functionalized olesoin incorporated in the vesicle. Binding and internalization of functionalized oleosin vesicles are performed in human umbilical vein endothelial cell culture, which possesses the α5β1 integrin receptor that RGDS and PHSRN target. Internalization and binding of vesicles is assessed using Nile Red labeled vesicles and confocal scanning microscopy. Also, combinations of bioactive molecules may be used. RDG, PHSRN and TAT peptides may be incorporated in any combination by making oleosins that possess them and mixing to see if combinations lead to enhanced binding and internalization.

Introduction of Protease Cleavable Domains to Backbone, and Measuring Release from Protease-Cleavable Vesicles:

Protease recognition sites (the oblique mark denotes the site of scission) for enterokinase (DDDDK/) (SEQ ID NO:8), Factor Xa (IEGR/) (SEQ ID NO:9), or thrombin (LVPR/G) (SEQ ID NO:11), are entrained in the amino acid sequence at the junction of hydrophilic and hydrophobic blocks, and at various positions in the hydrophilic arms. The principles of protease-mediated vesicle release are tested with both giant and nano-vesicles, which can be made through separate processing methods. Giant vesicles are reacted with the appropriate protease and monitored visually for signs of degradation. Quantitative kinetic information about the release is obtained by monitoring the rate of decrease of fluorescence of encapsulated fluorescent dyes. Confocal microscopy is used to image vesicles wherein a fluorophore is trapped in the vesicle interior or the oleosin is conjugated to a fluorophore at a specific position upstream of the protease site, so that protease action results in the fluorophore being cleaved. This can easily be achieved by adding a terminal lysine to that domain, and linking the N-terminus of the epsilon amine covalently with a fluorophore such as 5/6-carboxyfluorescein succinimidyl ester. For nanoscale vesicles, a decrease in size of the vesicles is detected through dynamic light scattering and confirmed with cryo-TEM. The site that may appear most logical for introduction of the protease recognition sequence may be relatively inaccessible to solvent. A library of such sites, with different locations of the protease cleavable domain, may need to be made in order to demonstrate vesicle degradation.

The delivery of particles to cells may be increased using targeting, but owing to the difficulty in modifying phospholipid vesicles and polymersomes, effective strategies for targeting vesicles to cells has been elusive. An oleosin vesicle that may be engineered so that its stability is critically impaired due to protease action opens the door to drug-delivery applications, where it would be desirable to have vesicles disintegrate upon encountering specific intracellular proteases. There are many proteases that are specific to individual cells (Camerer et al., 2000, PNAS 97(10):5255-5260), representing an additional mechanism for engineering delivery specifically to a target cell.

Pharmaceutical Compositions and Formulations

The invention also encompasses the use of pharmaceutical compositions of the proteins or vesicles of the invention or salts thereof to practice the methods of the invention.

Such a pharmaceutical composition may consist of at least one protein or vesicle of the invention or a salt thereof in a form suitable for administration to a subject, or the pharmaceutical composition may comprise at least one protein or vesicle of the invention or a salt thereof, and one or more pharmaceutically acceptable carriers, one or more additional ingredients, or some combination of these. The protein or vesicle of the invention may be present in the pharmaceutical composition in the form of a physiologically acceptable salt, such as in combination with a physiologically acceptable cation or anion, as is well known in the art.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina or any other tissue of a mammal Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a protein or vesicle of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alphatocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum *acacia*, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and *acacia*. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum *acacia* or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same disease as that treated by the compositions of the infection) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Routes of Administration

Routes of administration of any of the compositions of the invention include oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or *acacia*); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, *acacia*, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically-or naturally derived.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Vaginal Administration

A pharmaceutical composition of the invention may be prepared, packaged, or sold in a formulation suitable for vaginal administration. With respect to the vaginal or perivaginal administration of the compounds of the invention, dosage forms may include vaginal suppositories, creams, ointments, liquid formulations, pessaries, tampons, gels, pastes, foams or sprays. The suppository, solution, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, micro-particles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours. The term pulsatile release is used herein in its conventional sense to refer to a drug formulation that provides release of the drug in such a way as to produce pulsed plasma profiles of the drug after drug administration. The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Unless otherwise noted, all starting materials and reagents were obtained from commercial suppliers and used without purification. Sequence listings are illustrated in Table 1.

TABLE 1

| SEQ ID NO: | Name | Amino Acid Sequence |
|---|---|---|
| 1 | Oleo-WT Oleosin-1 | MATTTYDRHHVTTTQPQYRHDQHTGDRLT HPQRQQQGPSTGKIMVIMALLPITGILFGLA GITLVGTVIGLALATPLFVIFSPVIVPAMIAIG LAVTGFLTSGTFGLTGLSSLSYLFNMVRRST MSVPVQRDYVKGKLQDVGEYTGQKTKDL GQKIQHTAHEMGDQGQGQGQGGGKEGRK EGGKLEHEHHHH |

TABLE 1 -continued

| SEQ ID NO: | Name | Amino Acid Sequence |
|---|---|---|
| 2 | 25-87-40 Oleosin-2 Oleosin-hydrophobic | MRHDQHTGDRLTHPQRQQQGPSTGKIMVI MALLPITGILFGLAGITLVGTVIGLALATPLF VIFSPVIVPAMIAIGLAVTGFLTSGTFGLTGL SSLSYLFNMVRRSTMSVPVQRDYVKGKLQ DVGEYTGQKTKDLGQKIQHTAHEMGDQGL EHHHHHH |
| 3 | 42-65-57 Oleosin-3 Oleosin-hydrophilic | MATTTYDRHHVTTTQPQYRHDQHTGDRLT HPQRQQQGPSTGKITGILFGLTGITLVGTVIG LALATPLFVIFSPVIVPAMIAIGLAVTGFLTS GTFGLTRSTMSVPVQRDYVKGKLQDVGEY TGQKTKDLGQKIQHTAHEMGDQGQGQGQ GGGKEGRKEGGKLEHHHHHH |
| 4 | | RGDS |
| 5 | | PHSRN |
| 6 | | RKKRRQRRR |
| 7 | | GGGGS |
| 8 | | DDDDK |
| 9 | | IEGR |
| 10 | | ENLYQG |
| 11 | | LVPRG |
| 12 | | LPETG |
| 13 | 7-87-7 | MGSPSTGKIMVIMALLPITGILFGLAGITLVG TVIGLALATPLFVIFSPVIVPAMIAIGLAVTG FLTSGTFGLTGLSSLSYLFNMVRRSTMSVPV QRDYVLEHHHHHH |
| 14 | 7-87-57 | MGSPSTGKIMVIMALLPITGILFGLAGITLVG TVIGLALATPLFVIFSPVIVPAMIAIGLAVTG FLTSGTFGLTGLSSLSYLFNMVRRSTMSVPV QRDYVKGKLQDVGEYTGQKTKDLGQKIQH TAHEMGDQGQGQGQGGGKEGRKEGGKLE HHHHHH |
| 15 | 42-87-7 | MGSTTTYDRHHVTTTQPQYRHDQHTGDRL THPQRQQQGPSTGKIMVIMALLPITGILFGL AGITLVGTVIGLALATPLFVIFSPVIVPAMIAI GLAVTGFLTSGTFGLTGLSSLSYLFNMVRRS TMSVPVQRDYVLEHHHHHH |
| 16 | 12-87-27 | MGSRQQQGPSTGKIMVIMALLPITGILFGLA GITLVGTVIGLALATPLFVIFSPVIVPAMIAIG LAVTGFLTSGTFGLTGLSSLSYLFNMVRRST MSVPVQRDYVKGKLQDVGEYTGQKTKDL GQLEHHHHHH |
| 17 | 7-87-12 | MGSPSTGKIMVIMALLPITGILFGLAGITLVG TVIGLALATPLFVIFSPVIVPAMIAIGLAVTG FLTSGTFGLTGLSSLSYLFNMVRRSTMSVPV QRDYVKGKLQLEHHHHHH |
| 18 | 12-87-12 | MGSRQQQGPSTGKIMVIMALLPITGILFGLA GITLVGTVIGLALATPLFVIFSPVIVPAMIAIG LAVTGFLTSGTFGLTGLSSLSYLFNMVRRST MSVPVQRDYVKGKLQLEHHHHHH |
| 19 | 22-87-37 | MGSHTGDRLTHPQRQQQGPSTGKIMVIMAL LPITGILFGLAGITLVGTVIGLALATPLFVIFS PVIVPAMIAIGLAVTGFLTSGTFGLTGLSSLS YLFNMVRRSTMSVPVQRDYVKGKLQDVGE YTGQKTKDLGQKIQHTAHEMGLEHHHHHH |

TABLE 1 -continued

| SEQ ID NO: | Name | Amino Acid Sequence |
|---|---|---|
| 20 | 42-87-32 | GSTTTYDRHHVTTTQPQYRHDQHTGDRLT THPQRQQQGPSTGKIMVIMALLPITGILFGLA GITLVGTVIGLALATPLFVIFSPVIVPAMIAIG LAVTGFLTSGTFGLTGLSSLSYLFNMVRRST MSVPVQRDYVKGKLQDVGEYTGQKTKDL GQKIQHTLEHHHHHH |
| 21 | 7-65-7 | MGLNDIFEAQKIEWHEGSPSTGKIMGILFGL TGITLVGTVIGLALATPLFVIFSPVIVPAMIAI GLAVTGFLTSGTFGLTRSTMSVPVQRDYVL EHHHHHH |
| 22 | 12-65-12 | MGLNDIFEAQKIEWHEGSRQQQGPSTGKIT GILFGLTGITLVGTVIGLALATPLFVIFSPVIV PAMIAIGLAVTGFLTSGTFGLTRSTMSVPVQ RDYVKGKLQLEHHHHHH |
| 23 | 17-65-17 Oleosin mutant 1 Oleo-M1 | MGLNDIFEAQKIEWHEGSLTHPQRQQQGPS TGKITGILFGLTGITLVGTVIGLALATPLFVIF SPVIVPAMIAIGLAVTGFLTSGTFGLTRSTMS VPVQRDYVKGKLQDVGEYLEHHHHHH |
| 24 | 27-65-27 | MGLNDIFEAQKIEWHEGSYRHDQHTGDRLT HPQRQQQGPSTGKITGILFGLTGITLVGTVIG LALATPLFVIFSPVIVPAMIAIGLAVTGFLTS GTFGLTRSTMSVPVQRDYVKGKLQDVGEY TGQKTKDLGQHHHHHH |
| 25 | 42-65-7 | GLNDIFEAQKIEWHEGSTTTYDRHHVTTTQ PQYRHDQHTGDRLTHPQRQQQGPSTGKIM GILFGLTGITLVGTVIGLALATPLFVIFSPVIV PAMIAIGLAVTGFLTSGTFGLTRSTMSVPVQ RDYVLEHHHHHH |
| 26 | 7-65-57 | GLNDIFEAQKIEWHEGSPSTGKIMGILFGLT GITLVGTVIGLALATPLFVIFSPVIVPAMIAIG LAVTGFLTSGTFGLTRSTMSVPVQRDYVKG KLQDVGEYTGQKTKDLGQKIQHTAHEMGD QGQGQGQGGGKEGRKEGGKLEHHHHHH |
| 27 | 27-87-12 | GSYRHDQHTGDRLTHPQRQQQGPSTGKIM VIMALLPITGILFGLAGITLVGTVIGLALATP LFVIFSPVIVPAMIAIGLAVTGFLTSGTFGLT GLSSLSYLFNMVRRSTMSVPVQRDYVKGK LQLEHHHHHH |
| 28 | 22-87-12 | GSHTGDRLTHPQRQQQGPSTGKIMVIMALL PITGILFGLAGITLVGTVIGLALATPLFVIFSP VIVPAMIAIGLAVTGFLTSGTFGLTGLSSLSY LFNMVRRSTMSVPVQRDYVKGKLQLEHHH HHH |

Creating Oleosin-Like Protein Genes:

Standard PCR techniques were used to create the genes for the oleosin-like proteins (or variants). Sunflower seed oleosin was used as the foundation and specifically designed primers were used to create the genes. "Oleosin-hydrophobic" was created in a single PCR while "oleosin-hydrophilic" was created in multiple PCR steps. The gene was created in three pieces by running three separate PCR experiments. These pieces were connected using standard PCR techniques.

Expression of Oleosin-Like Proteins:

Standard molecular biology techniques were used to create the modified genes in the expression vector pBamUK, a pET series derivative. The *E. Coli* strain used for expression was BL21 DE3 with induction controlled by the lac promoter. Cultures were grown in Lysogeny Broth (LB) (Thermo) with Kanamycin antibiotic added to a final concentration of 50 mg/L. Cultures were incubated at 37° C. until $OD_{600}$~0.4. All cultures were constantly shaking at 225 rpm. Expression of the protein was induced by the addition of isopropyl β-D-thiogalactoside (IPTG) stock solution to a final concentration of 1.0 mM. The culture was grown for >3 hours at 37° C. The cells were harvested by centrifugation (15,000 g, 15 minutes). The cell pellets were frozen at −20° C. before purification.

Extraction of Oleosin-Like Proteins:

B-PER Protein Extraction Agent (Thermo Scientific) was used to extract the protein from the cell pellet according to the manufacturer's procedure with slight modification.

In one embodiment, a frozen cell pellet was suspended in 4 ml B-PER Protein Extraction Agent per gram of cell pellet. DNAse was added at a volume of 2 μl (2 mg/ml) per gram of cell pellet. The solution was vortexed until homogeneous and allowed to incubate at room temperature for 10 minutes, centrifuged (15,000 g, 15 minutes), and the supernatant was discarded. This procedure was repeated with lysozyme at a final concentration of 200 μg/ml. The pellet was washed with 50 ml (1:10 dilution of B-PER in water), centrifuged (15,000 g, 15 minutes), and the supernatant was discarded. The wash was repeated three times total leaving the inclusion body pellet. The inclusion bodies were solubilized in buffer A (8 M urea, 50 mM Phosphate buffer) for purification.

In one embodiment, the resulting pellet was washed twice with 50 ml 100 mM phosphate buffer (pH 7) to remove excess surfactant from BPEA. The pellet was further washed with 5 ml 200 mM $Na_2CO_3$ (pH 11) twice to remove excess DNA bound to the protein. Oleosin was extracted from the inclusion bodies using an organic solvent mixture as previously reported [43, 44]. The pellet was resuspended in 200 mM $Na_2CO_3$ (pH 11) by vortexing. Chloroform:methanol mixtures were added to the suspension yielding monophasic solutions of $Na_2CO_3$:chloroform:methanol ranging from 1:1:8 to 1:5:4 (v/v/v). The solutions were centrifuged at 15,000 g and the protein rich supernatant was retained.

Purification of Oleosin-Like Proteins:

In one embodiment, the oleosin-like proteins expressed were purified by immobilized metal-affinity chromatography (IMAC) through a six-histidine tag introduced for this purpose at the C-Terminus Protein purification using HisPur Ni-NTA resin (Thermo Scientific) was completed according to the manufacturer's procedure. Briefly, the Ni-NTA column was equilibrated by adding two bed volumes of buffer A. The column was centrifuged (700 g, 2 minutes) and the supernatant discarded. The soluble protein extract was added to the conditioned column and allowed to incubate at room temperature on an end-over-end mixer overnight. The mixture was centrifuged (700 g, 2 minutes) and the supernatant discarded. On-column refolding of the protein was completed by diluting the remaining resin in 100 ml PBS (Sigma) and stirring at 4° C. for >4 hours. The solution was centrifuged (700 g, 2 minutes) and supernatant discarded. The resin was washed with two resin-bed volumes of wash buffer (20 mM imidazole, 50 mM Phos, 300 mM NaCl) for 10 minutes at room temperature. The supernatant was discarded after centrifugation at 700 g (2 minutes). The wash was repeated three times. The protein was eluted in 500 µl fractions with elution buffer (300 mM imidazole, 50 mM Phos, 300 mM NaCl). $A_{280}$ was measured for each fraction using a NanoDrop ND-1000 Spectrophotometer (Thermo Scientific). Fractions were taken until a baseline $A_{280}$ was reached. The protein was dialyzed (Float-A-Lyzer G2, 500-1000 Da, Spectrum Labs), and the final solutions were lyophilized and stored at 4° C.

SDS-PAGE and Western Blotting:

Samples of protein solutions (1:1:8 to 1:5:4) were dried overnight under vacuum. The resulting protein pellets were suspended in 8M urea, 50 mM phosphate and used for electrophoresis. SDS-PAGE gels were run on NuPAGE Novex 4-12% BisTris Mini Gels (Invitrogen) according to the NuPAGE Technical Guide. Following electrophoresis, the gel was stained with SimplyBlue SafeStain (Invitrogen) according to the user guide. The gel was de-stained and imaged with a Kodak Gel Logic 100 Imaging System. For Western blotting, proteins were transferred from SDS-PAGE gel onto nitrocellulose membrane using an Invitrogen Novex Mini Cell System (Invitrogen) according to the manufacturer's instructions. Western blot analysis was completed according to Li-Cor Biosciences Western Blot Analysis protocol. Specifically, an anti-6-Histidine anti-mouse antibody (Covance) was used at a 1:2000 dilution as the primary antibody. The membrane was subjected to immunodetection using the secondary antibody IRDye 700DX conjugated goat polyclonal anti-mouse (Li-Cor) at a 1:5000 dilution. The membrane was imaged on an Odyssey Infrared Imager (Li-Cor Biosciences, Lincoln, Nebr.).

Vesicle Preparation:

Lyophilized protein in a 1.5 ml vial was suspended in a pure organic solvent (chloroform, or dichloromethane). In order to dye the membrane, the hydrophobic stain, Nile Red, was added to the organic solvent. The organic solvent was allowed to evaporate at ambient conditions for >8 hours and the vial was further dried in vacuum for >8 hours. The protein was suspended in water and sonicated in a Branson 3510 bath sonicator (Branson Ultrasonics, Danbury, Conn.) for 30 minutes at 45° C. to yield bilayer vesicles.

Nano-Vesicle Preparation:

Protein solutions in 1:1:8 ($Na_2CO_3$:chloroform:methanol) ranged from 0.25 to 0.5 mg/ml measured using a Nanodrop 100 (Thermo Scientific). The monophasic solutions were injected into deionized water at a volume fraction ranging from 5-10% and gently mixed until the solution turned clear.

Giant Vesicle Preparation:

Protein solutions in 1:2:7 ($Na_2CO_3$:chloroform:methanol) ranged from 0.25 to 0.5 mg/ml measured using a Nanodrop 100 (Thermo Scientific). The monophasic solutions were injected into deionized water at a volume fraction ranging from 5-10%. The injection resulted in phase separated aqueous in oil in aqueous double emulsions. The excess oil was allowed to evaporate at room temperature yielding stable vesicles. Giant vesicles were dyed by adding Nile Red and calcein (Invitrogen) to the injection mixture.

Dynamic Light Scattering:

Dynamic light scattering (DLS) measurements were made in deionized water on a Malvern Zetasizer NanoS (Malvern Instruments, Southboror, Mass.) instrument. Samples were prepared by a 100× dilution of the protein vesicle solution into deionized water.

Matrix-Assisted Laser Desorption/Ionization (MALDI) Mass Spectroscopy:

Protein solutions were dialyzed (0.5-1 kDa, Spectrum Labs) against 10 mM $NH_4HCO_3$. Protein samples were sent to The Wistar Institute Proteomics Facility (Philadelphia, Pa.) for mass analysis using matrix-assisted laser desorption/ionization (MALDI) mass spectroscopy.

Circular Dichroism:

Far-UV CD spectra were collected at 25° C. on an AVIV 410 spectrometer (AVIV Biomedical Inc, Lakewood, N.J.) using a 1 mm quartz cell. Protein concentrations ranged from 9-12 µM. Data was analyzed using DichroWeb software (Whitmore & Wallace, 2004, Nucl. Acids Res., 32:W668-W673) using the CDSSTR method and the SMP180 dataset (Sreerama et al., 2000, Anal. Biochem. 287(2):243-251; Abdul-Gader et al., 2011, Bioinform. 27(12):1630-1636).

Confocal Microscopy:

Laser scanning confocal microscopy (LSCM) was used to expose giant protein bilayer vesicles to light at 488 nm. An Olympus Fluoview FV1000 confocal microscope (Center Valley, Pa.) with a UPLFLN 40× oil objective lens was used to image the vesicles with a scan speed of 4.0 µs pixel (4.426 s frame$^{-1}$). Nile Red signal was collected between 600-650 nm and Calcein was collected between 500-520 nm.

Cryo-TEM:

Nano-vesicle samples were deposited on lacey formvar/carbon 200 mesh grid and added to a cryoplunger (Gatan Cp3, Gatan, Pleasanton, Calif.). The sample was blotted by hand and plunged into liquid ethane. Samples were transferred to the cryoholder (Gatan CT3500TR, Gatan, Pleasanton, Calif.) and the cryoholder was immediately inserted into a JEOL 2010 TEM (JEOL, Tokyo, Japan) operating at 200 kV. Samples were maintained at liquid nitrogen temperatures at all times. Micrographs were imaged with an Orius SC200 digital camera.

Micropipette Aspiration of Giant Vesicles:

Micropipette aspiration follows procedures originally described by Evans and Needham (Evans & Needham, 1987, J. Phys. Chem. 91:4219-4228). Micropipettes made of borosilicate glass tubing (Griedrich and Dimmock, Milville, N.J.) were prepared using a needle/pipette puller (model 730, David Kopf Instruments, Tujunga, Calif.) and microforged. Pipettes were filled with PBS solution and connected to an aspiration station on a Zeiss inverted microscope, equipped with a manometer, Validyne pressure transducers (models DP 15-32 and DP 103-14, Validyne Engineering Corp., Northridge, Calif.), digital pressure read-outs, micromanipulators (model WR-6, Narishige, Tokyo, Japan), and Melles-Griot millimanipulators (course x,y,z control). Suction pressure was applied via a syringe connected to the manometer. Membrane extensions and membrane diameter after aspiration will be analyzed with ImageJ software (Sheffield, 2007, Micr. & Microanal. 13:200-201) and used to calculate the area expansion modulus ($K_a$) from the slope of the membrane tension versus change in area.

Dye Encapsulation and Release:

Hydrophobic dye is loaded into the membrane as described above. Hydrophilic dye can be loaded in the aqueous solution by passive loading during the sonication step during the vesicle preparation. After dye loading, the vesicles are exhaustively dialyzed to remove excess dye. Release studies follow similar procedures as previously described (Katz et al, 2009, Langmuir 25(8):4429-34). Briefly, the release of dye is monitored by recording the fluorescence of protein vesicle solutions over time. The initial amount of dye encapsulated is calculated by bursting the vesicles with heat and surfactant and measuring the total fluorescence.

Binding and Internalization of Vesicles in HUVECs in Culture:

Human umbilical vein endothelial cells (HUVECs) is cultured in EGM Endothelial Growth Media (Lonza, Walkersville, Md.) supplemented with 0.4% bovine brain extract (BBE) with heparin, 0.1% h-EGF, 0.1% hydrocortisone, 0.1% gentamicin sulfate (GA-1000), and 2% fetal bovine serum (FBS). Cells are maintained in plastic culture flasks at 37° C. in a humidified atmosphere containing 5% $CO_2$ in air and subcultured when the flasks were 70% to 90% confluent. HUVECs are used between passages 5-7. HUVECs are harvested and plated on glass coverslips in custom-made incubation chambers, and Nile Red-labeled oleosin vesicles are added to the culture at different concentrations and various lengths of time. The internal labeling of cells is measured by confocal microscopy.

Example 1

Production of Recombinant Oleosins

Two oleosin-like proteins were created with different hydrophobic block fractions (FIG. 2) of sunflower seed oleosin—"oleosin-hydrophobic", SEQ ID NO:2; "oleosin-hydrophilic", SEQ ID NO:3. Hydrophobic block fractions were calculated by taking the ratio of amino acids in the central hydrophobic domain to the total number of amino acids in the sequence. The genes for the oleosin-like proteins were created by removing specific codons from sunflower seed oleosin gene through PCR. Oleosin-hydrophobic is an oleosin-like protein, which was made by removing amino acids from both the N- and C-terminus until the hydrophobic block fraction of the protein was about 50%. Oleosin-hydrophilic is an oleosin-like protein, which was made by removing amino acids from the central hydrophobic domain until the protein was about 67% hydrophilic. In all cases, the proline knot and 6-Histidine was conserved.

All variations of oleosin were expressed in inclusion bodies and yielded ~12-24 mg of purified protein/liter of culture after purification. The expected weights of the proteins, oleosin-philic and oleosin-phobic, were 18.4 and 17.1 kDa respectively (FIGS. 3A and 3B). The SDS-PAGE gel showed the purity of the protein after purification by immobilized metal-affinity chromatography (IMAC). Oleosin-hydrophilic and oleosin-hydrophobic homogeneity was examined by Western blotting using an antibody against the 6-Histidine tag on the protein (FIG. 3C). Both SDS-PAGE and Western blotting confirm the expected molecular weight of the proteins and show multimers of the protein in the purified solution.

Example 2

Protein Assembly into Vesicles

The oleosin-like proteins, oleosin-hydrophilic and oleosin-hydrophobic, were found to form bilayer vesicles in water. A non-limiting general schematic representation of how these molecules may assemble into bilayers is illustrated in FIG. 4. Without wishing to be limited by theory, it is contemplated that, because of the proline rich turn segment, single oleosin chains may not span the entire bilayer.

Figure 5:
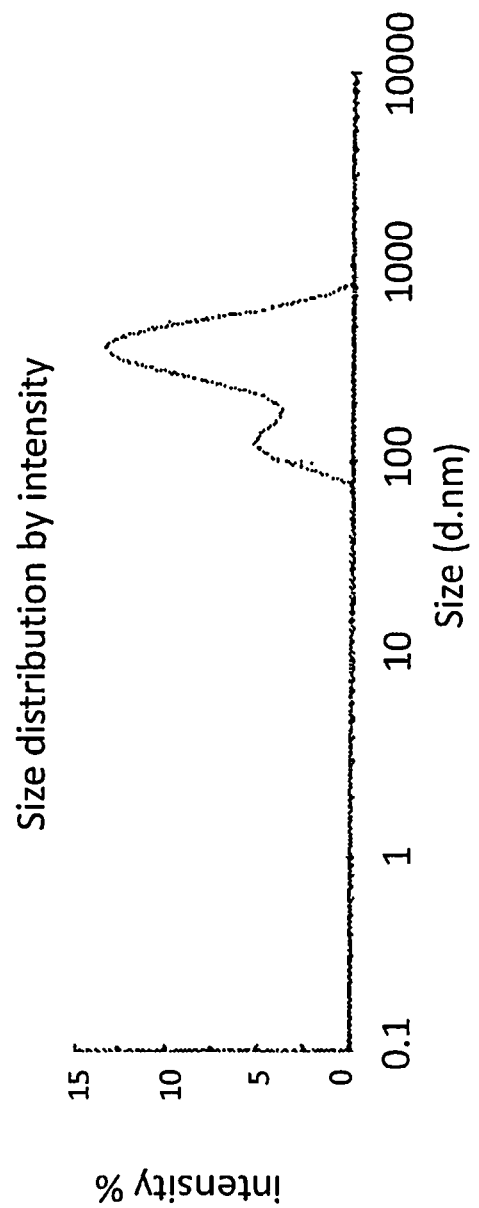
FIG. 5 is a graph illustrating dynamic light scattering performed on oleosin-hydrophobic vesicles in water (100× dilution). The average particle size is 370 nm with peaks at 140 nm and 390 nm.

To make vesicles, lyophilized protein is suspended in a high vapor pressure solvent (dichloromethane and chloroform) to ensure complete drying. After drying, the protein is hydrated with deionized water and sonicated at elevated temperature to create bilayer vesicles. Dynamic light scattering (DLS) shows that the average vesicles size of oleosin-hydrophobic vesicles to be 370 nm with peaks at 140 nm and 380 nm (FIG. 5). Cryo-transmission electron microscopy (Cryo-TEM) may be used to determine the structure of the nanosized particles.

Vesicles were loaded with the hydrophobic dye, Nile Red, by addition to the organic solvent before drying. The dye was soluble only in the hydrophobic regions of the structure. Upon hydration with deionized water, the dye remained in the hydrophobic membrane of the vesicles (FIG. 6). The encapsulation of Nile Red in the membrane indicates that the vesicle has a hydrophobic membrane and a hydrophilic lumen. This configuration suggests that the membrane is in a bilayer structure, and thus oleosin vesicles have been prepared. Measurements of the thickness of the membrane may be performed using CryoTEM.

Example 3

Preparation and Characterization of Vesicles with Recombinant Oleosin

Cryo-TEM may be used to evaluate effects of truncations or alterations of the oleosin structure in the protein's ability to assemble into membranes. Substitution or permutation of blocks of oleosin is also performed to generate novel proteins, and then the chemistry-structure relationship of these molecules is analyzed.

Oleosin is a hairpin molecule with two hydrophilic arms. Oleosin-like proteins are prepared using the following strategy: (a) perform serial truncations of either the N-terminal or C-terminal hydrophilic blocks and test the resulting protein for vesicle formation; (b) replace the hydrophobic chains and evaluate the importance of hydrophobic sequence on membrane formation and folding; and (c) replace the proline knot and investigate if membrane formation is adversely affected.

Serial truncations of each hydrophilic arm are performed to determine their importance in vesicle formation. It is typical in block-co-polymer systems to systematically map the phase diagram relating surfactant structure to self-assembled architecture. This may be accomplished through truncating each arm in five amino acid segments, and then both arms simultaneously, to map the phase diagram of vesicle formation. The ability of forming vesicles may be evaluated in terms of three parameters: the total molecular weight of the protein, the hydrophilic block fraction ($f_{HYDROPHILIC}$) and the ratio of the sizes of N-terminal and C-terminal arms of the protein hydrophiles ($a_N/a_C$). This additional parametric complexity may lead to a phase diagram relating peptide chemistry to structure. Structural determination may be corroborated at the nanoscale through cryo-TEM imaging.

Oleosin function may be relatively insensitive to the precise sequence of the hydrophobic block. Thus, the hydrophobic core may be replaced with alternate hydrophobic sequences such as hydrophobic elastin-like proteins (ELPs, e.g., $(VPGVG)_n$) or leucine zippers with or without the proline knot (elimination of the proline knot did not affect ER intercalation and, by inference, may not affect vesicle formation) to create hybrid membrane forming proteins. Once soluble expression is assured, vesicle formation may be examined for the variants created. As a specific example, sunflower oleosin may be truncated at T75 and a hydrophobic ELP, say, $(VPGVG)_n$ may be appended. In this molecular weight range, the ELP undergoes phase separation around 35° C. Vesicle formation may be temperature sensitive, although the transition temperature of the ELP may be affected significantly by the oleosin fusion; the ability of vesicles to self-assemble after the temperature is lowered may be evaluated. Hydrophilic ELPs fused to the hydrophobic oleosin core may also be examined Using leucine zippers as the hydrophobic domain may result in enhanced stability vis-a-vis wild-type vesicles and perhaps, in stronger vesicles, as assessed by micropipette aspiration.

Another approach comprises replacing the proline knot with a short or long linker composed of (-GGGGS-; SEQ ID NO:7) blocks. These linkers are known to be flexible and, if the 180° kink is smoothed out and allow the protein to relax, the protein might take on a tri-block architecture, spanning the entire membrane. (The removal of the proline knot, in vivo, was found to result in the oleosin spanning the entire ER membrane).

In all cases, the material properties of the resulting vesicles may be measured using micropipette aspiration. The area expansion modulus and critical areal strain before failure may be reported for each vesicle forming formulation.

Given that oleosin is a new vesicle-forming molecule, mapping the chemistry-structure relationship for this protein is essential for effective future engineering of peptide chemistry. The use of ELPs as fusion partners or hydrophobic core constituents may result in thermally-responsive oleosin constructs that are useful in constructing vesicles that disintegrate when exposed to temperature excursions.

Example 4

Addition of Peptide Binding Motifs to Oleosin for Enhanced Biofunctionality

In one aspect, receptor-binding motifs may be incorporated into the hydrophilic shell of the oleosin protein, and directly expressed and assembled into membrane structures. Vesicles may be thus assembled using a variety of cell-binding motifs.

Nucleotide stretches coding for the peptides of interest (the integrin receptor binding peptides RGDS (SEQ ID NO:4), PHSRN (SEQ ID NO:5), and a Tat peptide for cell penetration, RKKRRQRRR; SEQ ID NO:6) are appended to the N-terminus or C-terminus of oleosin or an oleosin-like protein using standard molecular biology techniques. The ability of expressed oleosins containing these motifs to form vesicles is then assessed. If these molecules do not make vesicles themselves, they may be mixed with different ratios of any of oleosin-like proteins prepared herein, and the degree of cell binding and penetration may be evaluated as a function of the percentage of functionalized oleosin incorporated in the oleosin vesicle. Binding and internalization of functionalized oleosin vesicles are performed in human umbilical vein endothelial cell culture, which possesses the $\alpha_5\beta_1$ integrin receptor that RGDS and PHSRN target. Internalization and binding of vesicles is assessed using Nile Red labeled vesicles and confocal scanning.

To the extent that oleosins are amphiphilic molecules with separate hydrophobic and hydrophilic modules that spontaneously segregate to the interface, they are tailor-made for the display of protein modules with interfacial functionality. N-terminal fusions to oleosin are not detrimental to oil body stabilization, but whether they might affect vesicle formation remains to be explored. The internalization or binding of functionalized oleosin vesicles may be studied with HUVECs in culture. The advantage in pursuing these fusions with oleosin vesicles is that the peptides may be genetically fused to the termini, or interpolated at locations within the N- and C-terminal hydrophilic domains. Additionally, different peptides can be fused to the N- and C-domains for a truly multi-functional vesicle. For example, attachment of the TAT peptide on one arm and the attachment of an RGD peptide on the other arm may lead to enhanced cell binding and permeation.

Example 5

Addition of Cysteine Residues for Crosslinking

There is ample evidence with polymersomes that crosslinking of the polymeric molecules strengthens vesicles. In the context of protein vesicles, crosslinking may be most easily accomplished by forming disulfide bonds between cysteines or the oxidating neighboring tyrosines.

Sunflower oleosin has no cysteines. At least two cysteines are needed per molecule to effect continuous cross-linking. The location of the cysteines is of importance in order to minimize intramolecular crosslinks in favor of intermolecular links. A library of oleosins with multiple cysteines (since oleosin structure is not known at this time) may be prepared to determine optimal cysteine locations for extended crosslinking. Crosslinking may be achieved through oxidants such as oxidized glutathione or ferricyanide. If sufficiently hydrophobic oxidizing reagents are used, it may be possible to oxidize the cysteines in situ after vesicle formation. Alternatively, the protein may be oxidized in solution and then vesicles may be formed.

Like cysteines, tyrosine residues may also be crosslinked. Sunflower oleosin has four tyrosines, two in each of the terminal domains. There are no tyrosines in the hydrophobic domain. These tyrosine residues may be converted to L-3,4-dihydroxyphenylalanine (L-DOPA) using mushroom tyrosinase in borate buffer. The DOPA will then be oxidatively crosslinked using sodium periodate and ascorbic acid. The cross-linking of the tyrosines in the terminal domains may have similar effects as stabilization of oil bodies by polyoleosins (multimers up to hexamers were constructed genetically with head-to-tail linkers), which afforded enhanced protease resistance and thermal stability. In another aspect, one of the amino acids in the proline knot may be replaced with a tyrosine. Since the vesicle bilayer likely comprises two oleosins with the proline knots in proximity, conversion of tyrosine residues to DOPA and oxidation should result in "radial" strengthening of the vesicle wall, rather than the "circumferential" one described earlier. The vesicles may be quantitatively characterized using micropipette aspiration and other techniques to determine exactly how these cross-linked vesicles differ from each other and wild-type.

Polyoleosins have been shown to confer enhanced stability to oil bodies, when compared to monomeric oleosins. Expansion of cross-linking beyond the hexamer (the potential limit of genetic approaches) may be used to evaluate whether vesicle strength is further increased by increasing cross-linking.

Example 6

Introduction of Protease Cleavable Domains in Oleosin Backbone, and Release of Encapsulated Materials from Protease-Cleavable Vesicles Vesicle formation in polymersomes and in small molecule systems occurs when the hydrophilic fraction, $f_{HYDROPHILIC}$, is approximately 0.35±0.10. As $f_{HYDROPHILIC}$ falls below this value, the vesicles transform into micelles. Although this value may not be the same for oleosin vesicles, $f_{HYDROPHILIC}$ for vesicle formation may be assessed according to the experiments described above.

Degradation of the hydrophilic fraction by protease action may trigger vesicle degradation. The experiments described above help evaluate how truncations in the hydrophilic segments may lead to failure to form vesicles (i.e., determination of the critical ratio of $a_N/a_C$ required for membrane formation). Cleavage at the junction between hydrophilic and hydrophobic domains may lead to vesicle destabilization (Katz et al., 2010, J. Am. Chem. Soc. 132(11):3654). However, such protease cleavable domains might be inaccessible to proteases. The location of protease domains necessary to induce vesicle failure should thus be investigated. Changes in the $a_N/a_C$ ratio might be sufficient to induce membrane destabilization.

Optimized oleosins identified in the experiments described above are constructed. Protease recognition sites (the oblique mark denotes the site of scission) such as those for enterokinase (DDDDK/; SEQ ID NO:8), Factor Xa (IEGR/; SEQ ID NO:9), tobacco etch virus protease (ENLYQ/G; SEQ ID NO:10), thrombin (LVPR/G; SEQ ID NO:11), or the transpeptidase Sortase A (LPET/G; SEQ ID NO:12) are entrained in the amino acid sequence at the junction of hydrophilic and hydrophobic blocks, and at various positions along the hydrophilic sequence. Giant vesicles are reacted with the appropriate protease and monitored visually for signs of degradation. If the experiment is successful, more quantitative kinetic information may be obtained by, e.g., monitoring the rate of decrease of fluorescence of encapsulated fluorescent dyes. A flow cytometry experiment may be performed on vesicles wherein the oleosin is conjugated to a fluorophore at a specific position upstream of the protease site so that protease action result in the fluorophore being cleaved. This may be easily achieved by adding a terminal lysine to that domain, and linking the N-terminus of the epsilon amine covalently with a fluorophore. For nanoscale vesicles, a decrease in size of the vesicles is detected through scattering and correlated with a decrease in fluorescence in the same population, confirming that the vesicles undergoing proteolysis are in fact losing fluorescence. The site that seems appropriate for introduction of the protease recognition sequence may be relatively inaccessible to solvent, so a library of such sites may be made to demonstrate vesicle degradation by protease action.

A demonstration that an oleosin vesicle can be engineered, such that its stability is critically impaired due to protease action, opens the door to drug delivery applications, where it would be desirable to have vesicles disintegrate upon encountering intracellular proteases. Such a disruptive mechanism is most easily introduced in a protein vesicle where the recognition site can simply be genetically entrained in the amino acid sequence.

Example 7

Protein Design

Standard molecular biology techniques were used to create the sunflower seed oleosin gene. Wild-type oleosin (Oleo-WT; SEQ ID NO:1) has 42 hydrophilic amino acids in the C-terminus, 87 amino acids in the hydrophobic block, and 57 hydrophilic amino acids in the N-terminus From Oleo-WT, a mutant, Oleosin mutant 1 (Oleo-M1; SEQ ID NO:23) was constructed by removing 25 and 40 amino acids in the C- and N-terminal hydrophilic arms respectively, and removing 22 amino acids in the hydrophobic block of Oleo-WT (FIG. 7).

The protein has been defined in three sections: N and C are the N- and C-terminal hydrophilic arms respectively and H is the hydrophobic section. N-H-C defines the number of amino acids in each block. The hydrophobic block is bifurcated by a conserved proline knot. Oleo-M1 is a lower molecular weight protein with a higher hydrophobic fraction compared to Oleo-WT. All charged residues reside in the hydrophilic arms, N and C. By changing the molecular weight and number of residues kept in the hydrophilic arms, the isoelectric point (pI) of the protein could be controlled. Oleo-WT has a calculated pI of ~10 whereas the pI of Oleo-M1 was lowered to ~6.9 by eliminating several charged residues at the termini of the hydrophilic segments and decreasing the molecular weight.

Recombinant Production and Purification

Figure 8C:
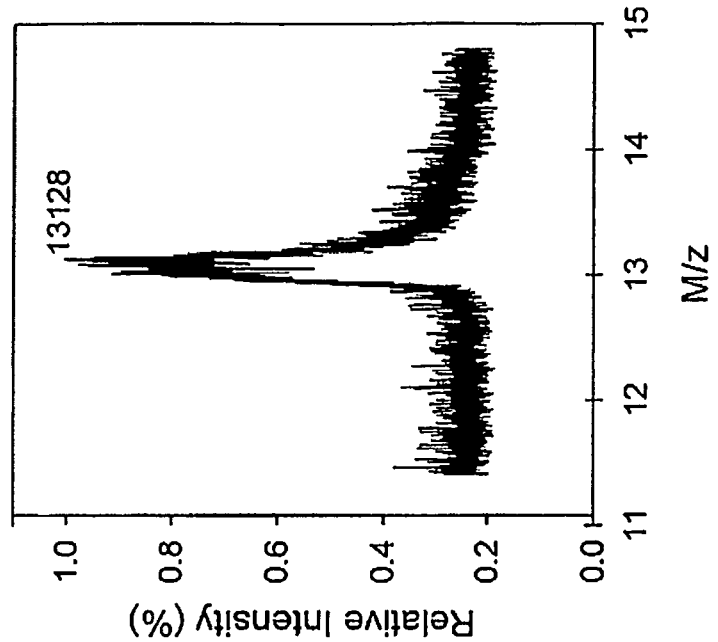
Figure 8B:
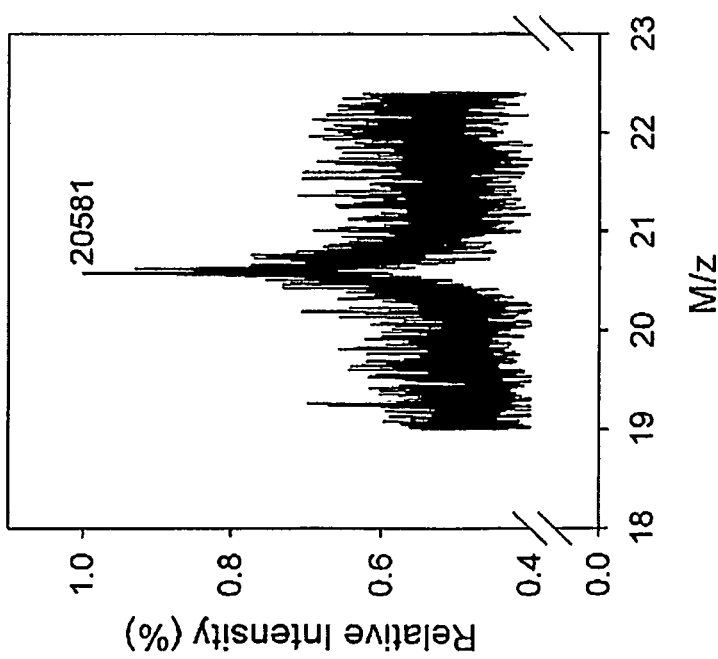

Oleo-WT and Oleo-M1 genes for bacterial expression were created using standard PCR techniques and cloned into the expression vector, pBamUK, which added a poly-histidine tag at the C-terminus for IMAC purification. SEQ ID NO: 21-25 were cloned into pBamUK-avi, which added a biotin binding site on the N-terminus IMAC purification was tested and found to have lower yield and similar purity compared to organic purification. The lac promoter controlled protein expression. Both proteins of interest were expressed in inclusion bodies. SDS-PAGE (FIG. 8) shows the purity of the overexpressed protein after purification in various organic solvents. Matrix-assisted laser desorption/ionization (MALDI) mass spectroscopy confirms the expected molecular weight of Oleo-WT and Oleo-M1 to be 20.6 and 13.1 kDa respectively (FIG. 8). High noise in the Oleo-WT spectrum is consistent with previous data showing interaction between the large hydrophobic domain of oleosin and the mass spectroscopy matrix (Alexander et al., 2002, Planta 214(4):546-551).

Protein Characterization

Figure 9A:
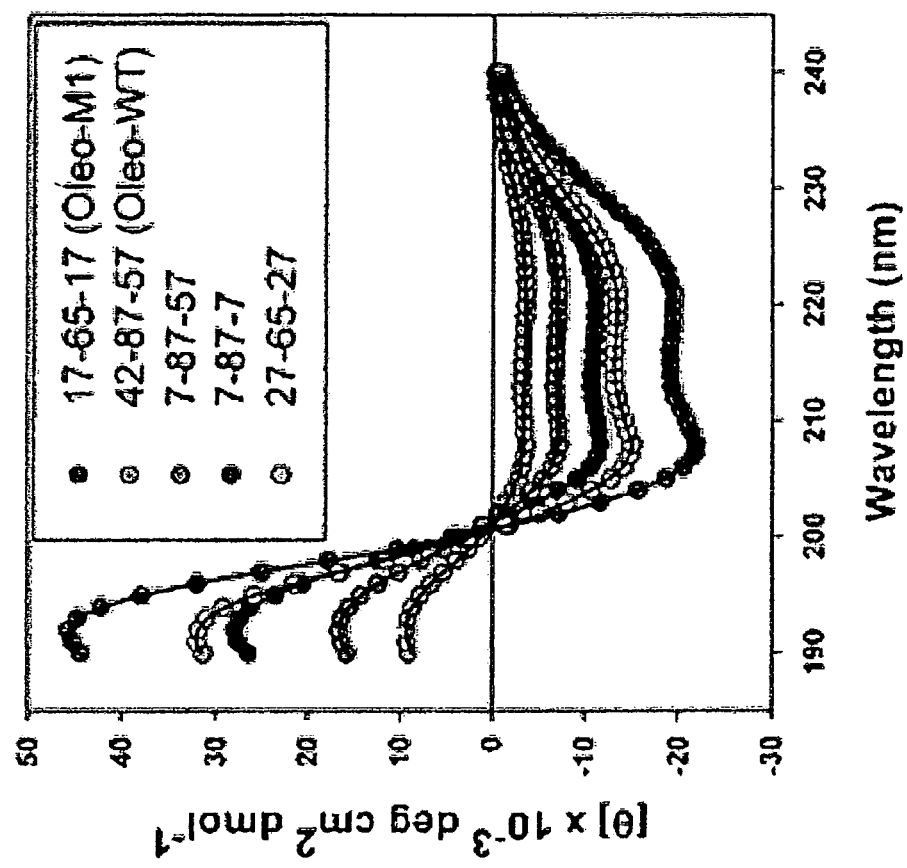

Removal of the hydrophilic sections has suggested that the hydrophobic section has significant alpha helical structure. Protein secondary structure, and its role (in addition to molecular weight and block size) in self-assembly, was explored using circular dichroism (FIG. 9), using standard structural analysis software (DichroWeb; Whitmore & Wallace, 2004, Nucleic Acids Res. 32:W668-W673). The truncation of Oleo-WT led to increased helical structure and decreased sheet structure. The protein secondary structure may affect the formation of bilayer membranes.

Self-Assembly of Protein Structures

Figure 10C:
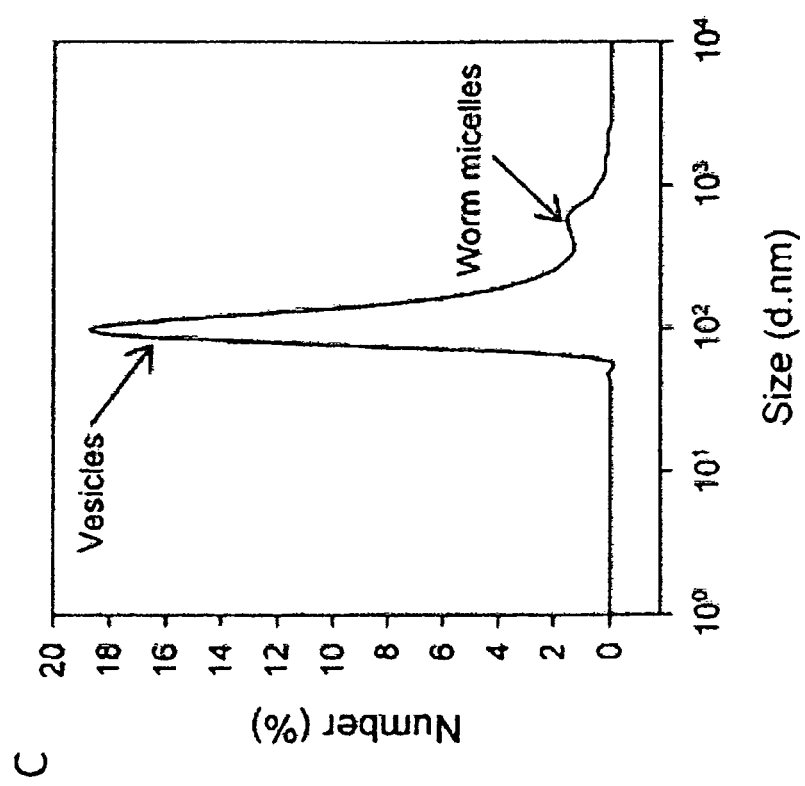
Figure 11B:
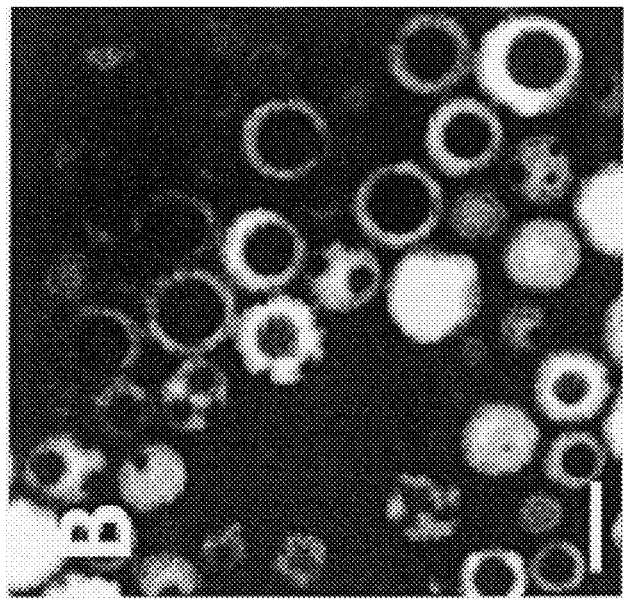
FIGS. 11A-11F, illustrates LSCM images of injected Oleo-M1 (17-65-17) in 1:2:7 (200 mM $Na_2CO_3$:chloroform:methanol) (v/v/v) into DI water and dried vesicles. Nile red and calcein were loaded in the injection mixture. Nile Red phase separated into the hydrophobic membrane and calcein remained in they hydrophilic lumen indicative of a bilayer vesicle.
Figure 11A:
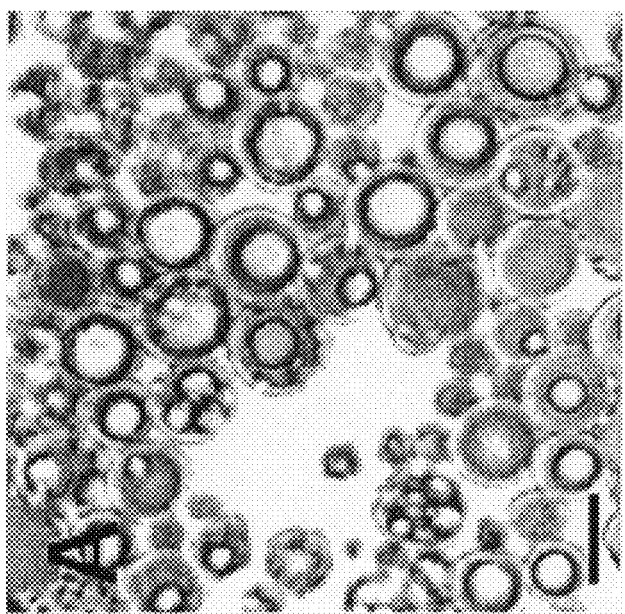
Figure 11C:
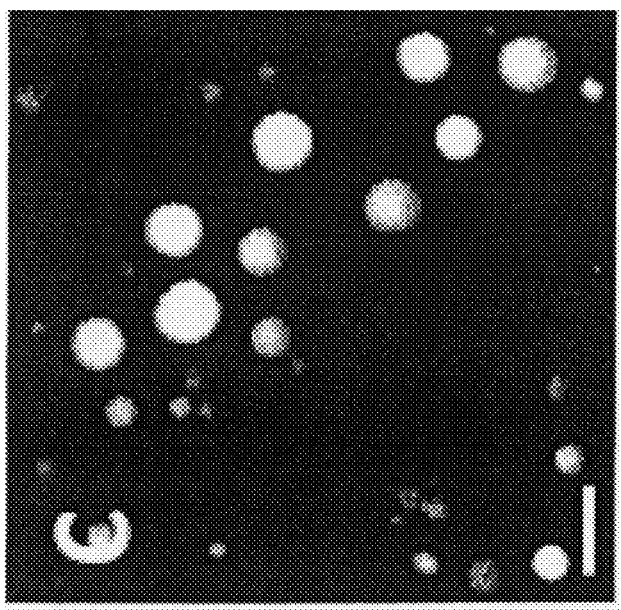
Figure 11D:
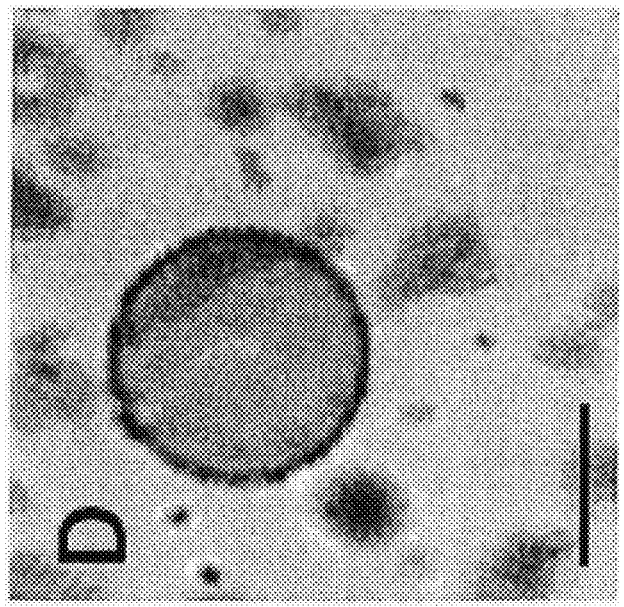
Figure 11F:
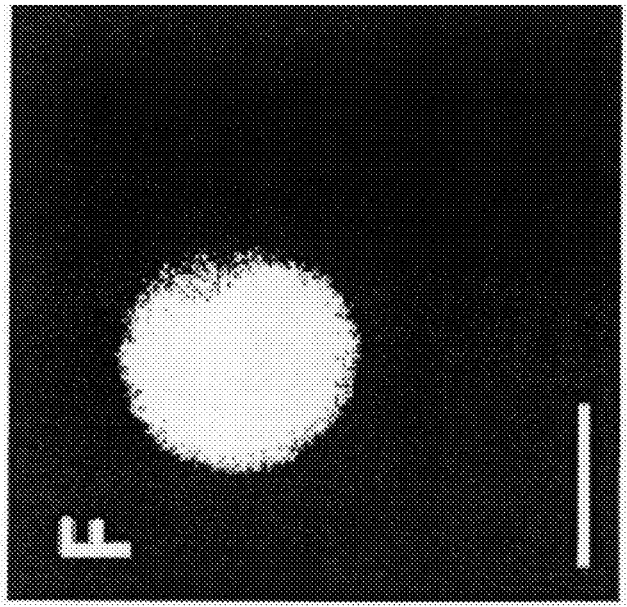
Figure 11E:
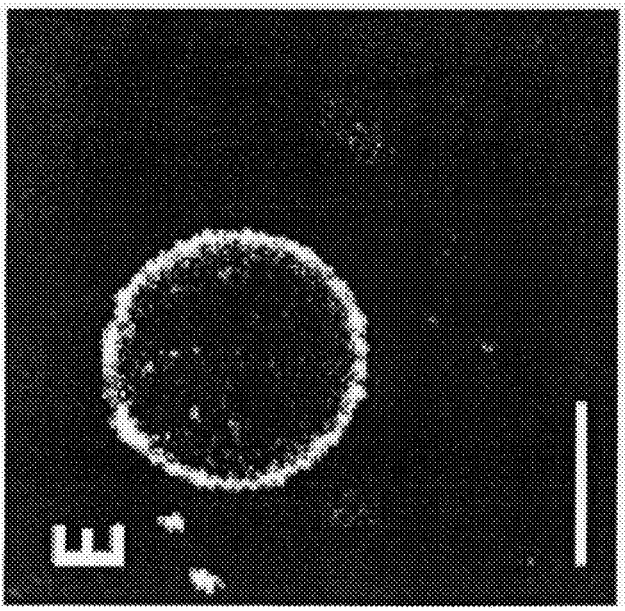

Sonication and thin film rehydration resulted in lower yield and protein aggregation whereas solvent injection resulted in the self-assembly of protein structures. Monophasic organic supernatants were injected directly into deionized water leading to self-assembled structures. The optimal injection solution for nano-vesicles was found to be 1:1:8 200 mM $Na_2CO_3$:chloroform:methanol (v/v/v). Cryo-TEM was used to determine the morphology of the structures. Cryo-TEM provides enhanced insight into the structural morphology compared to freeze fracture TEM, which does not show a membrane, and potential staining artifacts seen in TEM with negative staining. The injections of Oleo-M1 (1:1:8) into water led to the formation of vesicles and rod structures (FIG. 10). White blemishes indicated charging of the protein molecules leading to melting of the vitrified ice. Dark blemishes were ice crystals on top of the vitrified film. Vesicles membrane thickness was measured to be 39±4.4 nm (n=5, Cryo-TEM) and the tubular diameter was measured to be 25.9±3.4 nm (n=5, Cryo-TEM). Vesicle thicknesses greatly exceeded those seen in liposomes and polymersomes but matched expected values based on the hairpin structure of oleosin and the secondary structure calculated in circular dichroism. Dynamic light scattering (DLS) confirmed the relative vesicle diameter and the presence of larger hydrodynamic morphologies indicative of tubular structures (FIG. 10). Giant vesicles (>1 μm in diameter) were created using phase-separated double emulsions. (Both nano vesicles and giant vesicles could be made from the same proteins by different processing techniques, as also seen in phospholipid vesicles and polymersomes). Protein solutions (1:2:7 200 mM $Na_2CO_3$:chloroform:methanol) (v/v/v) were injected into deionized water. As the protein assembled at the chloroform-water interface, the monophasic mixture became unstable leading phase separation creating an aqueous in oil in aqueous double emulsion. Laser scanning confocal microscopy (LSCM) was used to image the original double emulsions and the bilayer vesicles created after drying (FIG. 11). Nile Red and calcein were added to the injection mixture. As the double emulsion dried, Nile Red sequestered into the hydrophobic membrane, whereas calcein remained in the hydrophilic lumen. Solutions with higher chloroform content (1:4:5 and 1:5:4) led to stable chloroform in water single emulsions (data not shown).

The capability to create mutant genes, express and purify the protein, and form vesicles was herein illustrated. This is the first report of vesicles created from recombinant proteins (>15 amino acids). This data sets the foundation for optimization of the protein for vesicle formation and the ability to create functional and responsive vesicles.

Example 8

Mutants of Oleosin

Figures 12A, 12B:
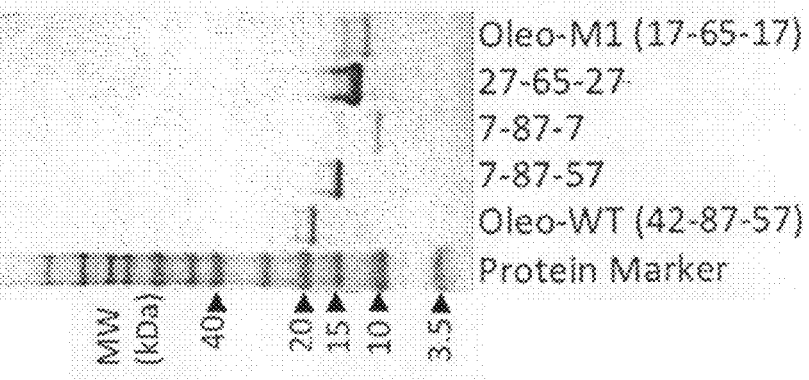
FIGS. 12A-12B, illustrates oleosin proteins.

In addition to Oleo-WT and Oleo-M1, other mutants of the parent molecule were created, expressed and purified in the same fashion. Mutations were made in the parent molecule's DNA through standard PCR techniques. 42-87-57 represents the wild type molecule (Oleo-WT). A total of 17 mutants were made and expressed to date. The gel in FIG. 12 shows several of these mutants and their purity. Therefore, oleosin and its mutants may be widely expressed and purified.

Figure 13:
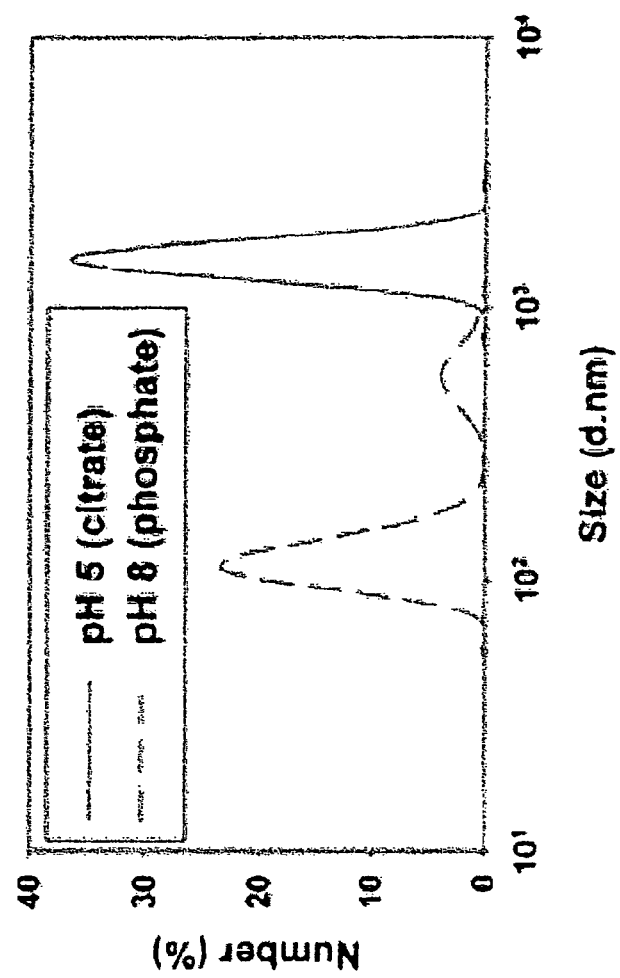
FIG. 13 is a graph illustrating dynamic light scattering data, showing number average size of protein structures after injection of Oleo-M1 (1:1:8) into two different pH buffers (10 mM).
Figure 14B:
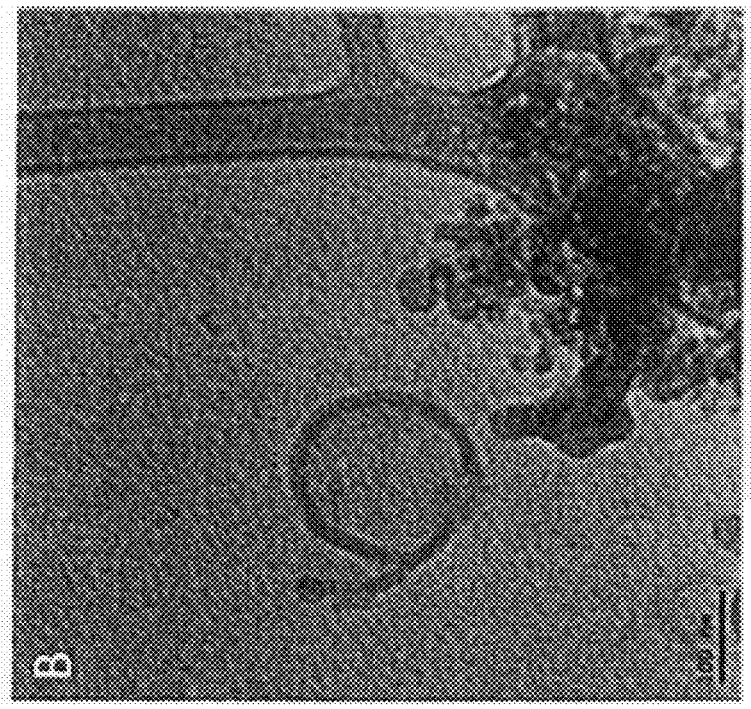
Figure 14A:
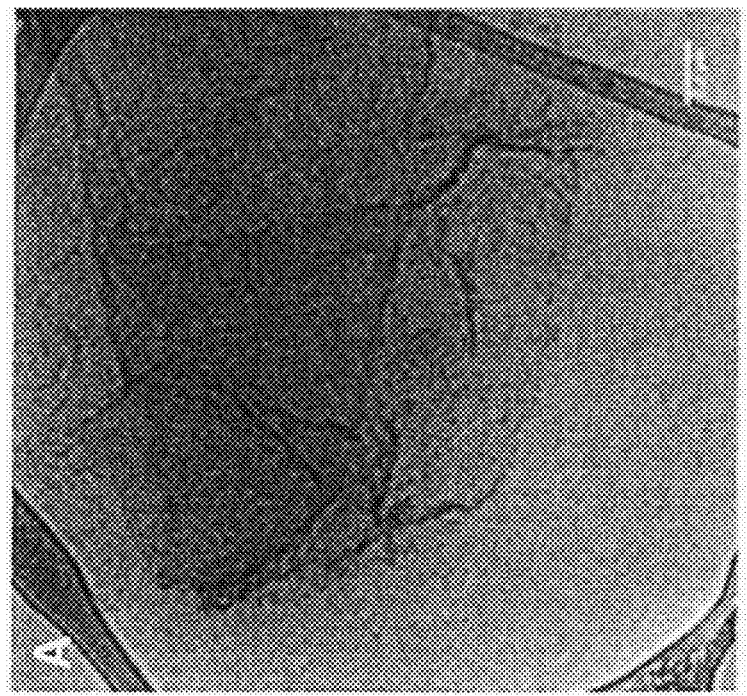

The isoelectric point (pI) of the protein mutants varies due to the number of charged amino acids in the hydrophilic arms and the overall molecular weight. The effective head group area may be changed by altering the pH of the solution. At a pH equal to the pI, the head group area is expected to be minimized because the net charge of the protein is expected to be zero. Oleo-M1 has an estimated pI of ~6.8. Histidine is the only amino acid whose side group pKa falls within this physiologic range. Therefore, Oleo-M1 in pH solutions below the pI leads to the protonation of histidine and a high positive charge on the protein. Solutions above the pI lead to the neutralization of histidine and an overall low net charge on the protein. DLS showed injections of Oleo-M1 (1:1:8 organic mixture) below the pI led to aggregation, whereas injections above the pI allowed for assembly (FIG. 13). Therefore, minimizing the effective head group size led to self-assembled structures; this has been shown for pH values 4-10 for Oleo-M1.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a protein comprising a sequence that has at least 80% homology to an oleosin-like protein selected from the group consisting of SEQ ID NOs: 21-26, and combinations thereof, wherein said protein is capable of self-assembling into a polypeptide vesicle.

2. The composition of claim 1, wherein said sequence has at least 90% homology to an oleosin-like protein selected from the group consisting of SEQ ID NOs:21-26, and combinations thereof.

3. The composition of claim 2, wherein said sequence has at least 95% homology to an oleosin-like protein selected from the group consisting of SEQ ID NOs:21-26, and combinations thereof.

4. The composition of claim 1, wherein a receptor binding motif is attached to the N-terminus or the C-terminus of said sequence via an amide bond.

5. The composition of claim 4, wherein said motif is selected from the group consisting of SEQ ID NOs:4-6.

6. The composition of claim 1, wherein at least two residues of said oleosin-like protein are replaced with cysteine residues.

7. The composition of claim 1, wherein at least one tyrosine residue in said oleosin-like protein is converted to a L-DOPA residue via a chemical reaction.

8. The composition of claim 7, wherein at least two of said L-DOPA residues are further crosslinked via a chemical reaction.

9. The composition of claim 1, wherein at least one sequence selected from the group consisting of SEQ ID NOs: 8-12 is inserted in said oleosin-like protein (i) at the junction of hydrophilic and hydrophobic segments, or (ii) within the hydrophilic segment.

10. A composition comprising a vesicle, wherein said vesicle comprises a protein comprising a sequence that has at least 80% homology to an oleosin-like protein selected from the group consisting of SEQ ID NOs:21-26, and combinations thereof.

11. The composition of claim 10, further comprising a compound encapsulated within said vesicle, wherein said compound is selected from the group consisting of a gas, drug, fluorescent dye, radioactive probe, salt, protein, and nucleic acid.

12. The composition of claim 10, further comprising at least one pharmaceutically acceptable carrier.

13. A composition comprising a protein comprising a peptide sequence as set forth in residues 26-88 of SEQ ID NO:21, wherein said protein is capable of self-assembling into a polypeptide vesicle.

* * * * *